(12) United States Patent
Hartung et al.

(10) Patent No.: US 9,451,909 B2
(45) Date of Patent: Sep. 27, 2016

(54) SYSTEM AND METHOD FOR DETECTING AMYLOID PROTEINS

(71) Applicant: Cognoptix, Inc., Concord, MA (US)

(72) Inventors: Paul D. Hartung, Acton, MA (US); Vincent Valvo, Southborough, MA (US); Charles Kerbage, Boston, MA (US); Gerald D. Cagle, Fort Worth, TX (US); Dennis J. Nilan, Milford, MA (US)

(73) Assignee: Cognoptix, Inc., Concord, MA (US)

(*) Notice: Subject to any disclaimer, the term of this patent is extended or adjusted under 35 U.S.C. 154(b) by 0 days.

(21) Appl. No.: 14/955,853

(22) Filed: Dec. 1, 2015

(65) Prior Publication Data

US 2016/0183859 A1    Jun. 30, 2016

Related U.S. Application Data

(63) Continuation of application No. 13/814,677, filed as application No. PCT/US2011/047628 on Aug. 12, 2011, now Pat. No. 9,220,403.

(60) Provisional application No. 61/374,131, filed on Aug. 16, 2010, provisional application No. 61/425,490, filed on Dec. 21, 2010.

(30) Foreign Application Priority Data

Feb. 11, 2011   (EP) ...................................... 11001148

(51) Int. Cl.
*A61B 3/10*      (2006.01)
*A61B 3/00*      (2006.01)
(Continued)

(52) U.S. Cl.
CPC ......... *A61B 5/14546* (2013.01); *A61B 3/0008* (2013.01); *A61B 3/1005* (2013.01);
(Continued)

(58) Field of Classification Search
CPC .. A61B 3/103; A61B 3/1225; A61B 3/1015; A61B 3/14; A61B 3/113; A61B 3/1208; A61B 3/024
USPC ............... 351/200, 205, 221, 246, 204, 206, 351/209–210, 215, 218, 222
See application file for complete search history.

(56) References Cited

U.S. PATENT DOCUMENTS 4,209,225 A    6/1980   Abe et al.
4,529,556 A    7/1985   Bruza
(Continued)

FOREIGN PATENT DOCUMENTS

DE   10 2007 061 987 A1   6/2009
EP        0 628 281 A1    6/1994
(Continued)

OTHER PUBLICATIONS

Notification of Transmittal of the International Search Report and the Written Opinion of the International Searching Authority, or the Declaration for International Application No. PCT/US2013/069598, date of mailing: Jul. 31, 2014, entitled: "Method for Measuring Fluorescence in Ocular Tissue".
(Continued)

*Primary Examiner* — Dawayne A Pinkney
(74) *Attorney, Agent, or Firm* — Hamilton, Brook, Smith & Reynolds, P.C.

(57) ABSTRACT

In accordance with an embodiment of the invention, there is provided a device and method for detecting an amyloid protein in an eye of a mammal. A method comprises illuminating the eye with a light source having at least one of a wavelength property, a polarization property or a combination thereof, each appropriate to produce fluorescence in at least an amyloid-binding compound when the amyloid-binding compound is bound to the amyloid protein, the amyloid-binding compound having been introduced to the eye and specifically binding to the amyloid protein indicative of the amyloidogenic disorder; and determining a time decay rate of fluorescence for at least the fluorescence produced by the amyloid-binding compound bound to the amyloid protein, the determining permitting distinguishing of the presence of the amyloid-binding compound bound to the amyloid protein in the eye based on at least the time decay rate.

58 Claims, 12 Drawing Sheets

(51) Int. Cl.
*A61B 3/14* (2006.01)
*A61B 5/145* (2006.01)
*A61B 5/1455* (2006.01)
*A61B 5/00* (2006.01)
*A61B 3/107* (2006.01)

(52) U.S. Cl.
CPC ............ *A61B 3/107* (2013.01); *A61B 5/1455* (2013.01); *A61B 5/4088* (2013.01); *A61B 2562/0238* (2013.01); *A61B 2562/0242* (2013.01)

(56) References Cited

U.S. PATENT DOCUMENTS

| | | |
|---|---|---|
| 4,702,576 A | 10/1987 | Magnante |
| 4,761,071 A | 8/1988 | Baron |
| 4,806,004 A | 2/1989 | Wayland |
| 4,957,113 A | 9/1990 | Benedek |
| 4,993,827 A | 2/1991 | Benedek et al. |
| 5,013,146 A | 5/1991 | Akiyama |
| 5,048,946 A | 9/1991 | Sklar et al. |
| 5,183,044 A | 2/1993 | Nishio et al. |
| 5,184,157 A | 2/1993 | Ichihashi et al. |
| 5,400,091 A | 3/1995 | Okazaki |
| 5,427,094 A | 6/1995 | Thurston et al. |
| 5,540,226 A | 7/1996 | Thurston et al. |
| 5,787,890 A | 8/1998 | Reiter et al. |
| 5,864,382 A | 1/1999 | Soya et al. |
| 5,880,813 A | 3/1999 | Thall |
| 5,894,340 A | 4/1999 | Loree et al. |
| 5,973,779 A | 10/1999 | Ansari et al. |
| 6,045,503 A | 4/2000 | Grabner et al. |
| 6,088,606 A | 7/2000 | Ignotz et al. |
| 6,096,510 A | 8/2000 | Hochman |
| 6,179,422 B1 | 1/2001 | Lai |
| 6,229,907 B1 | 5/2001 | Okano et al. |
| 6,280,386 B1 | 8/2001 | Alfano et al. |
| 6,299,305 B1 | 10/2001 | Miwa |
| 6,329,531 B1 | 12/2001 | Turner et al. |
| 6,419,361 B2 | 7/2002 | Cabib et al. |
| 6,478,424 B1 | 11/2002 | Grinvald et al. |
| 6,605,081 B1 | 8/2003 | Shimmick et al. |
| 7,147,328 B2 | 12/2006 | Sugino et al. |
| 7,303,281 B2 | 12/2007 | Wakil et al. |
| 7,452,078 B2 | 11/2008 | Isogai |
| 7,828,436 B2 | 11/2010 | Goldstein et al. |
| 8,388,134 B2 | 3/2013 | Goldstein et al. |
| 8,439,501 B2 | 5/2013 | Newman et al. |
| 8,955,969 B2 | 2/2015 | Hartung et al. |
| 9,220,403 B2 | 12/2015 | Hartung et al. |
| 2002/0091321 A1 | 7/2002 | Goldstein et al. |
| 2002/0157120 A1 | 10/2002 | Tsien et al. |
| 2002/0159947 A1 | 10/2002 | Zaczek et al. |
| 2002/0177778 A1 | 11/2002 | Averback et al. |
| 2003/0090626 A1 | 5/2003 | Lai et al. |
| 2004/0116811 A1 | 6/2004 | Koschmieder |
| 2004/0152068 A1 | 8/2004 | Goldstein et al. |
| 2004/0254154 A1 | 12/2004 | Ashton |
| 2004/0267118 A1 | 12/2004 | Dawson |
| 2005/0007551 A1 | 1/2005 | Walkil et al. |
| 2006/0176479 A1 | 8/2006 | Laurence et al. |
| 2007/0171366 A1 | 7/2007 | Su et al. |
| 2008/0088795 A1 | 4/2008 | Goldstein et al. |
| 2008/0227767 A1 | 9/2008 | Szarek et al. |
| 2010/0048510 A1 | 2/2010 | Eisenberg et al. |
| 2011/0060138 A1 | 3/2011 | Elmaleh et al. |
| 2011/0116041 A1 | 5/2011 | Hartung et al. |
| 2013/0114042 A1 | 5/2013 | Goldstein et al. |
| 2013/0135580 A1 | 5/2013 | Hartung et al. |

FOREIGN PATENT DOCUMENTS

| | | |
|---|---|---|
| EP | 0 983 757 A2 | 9/1999 |
| EP | 1913866 A1 | 4/2008 |
| EP | 2 268 193 | 1/2011 |
| EP | 2420179 A2 | 2/2012 |
| GB | 2 407 378 A | 4/2005 |
| GB | 2 409 033 A | 6/2005 |
| JP | 2009-264787 | 11/2009 |
| WO | WO 92/11799 | 7/1992 |
| WO | WO 94/06346 | 5/1994 |
| WO | WO 95/00068 | 1/1995 |
| WO | WO 95/13010 | 5/1995 |
| WO | WO 95/13011 | 5/1995 |
| WO | WO 99/18868 | 4/1999 |
| WO | WO 00/56204 | 9/2000 |
| WO | WO 02/16951 A2 | 2/2002 |
| WO | WO 02/064031 A2 | 8/2002 |
| WO | WO 03/018068 A1 | 3/2003 |
| WO | WO 03/032823 A2 | 4/2003 |
| WO | WO 03/090613 A1 | 11/2003 |
| WO | WO 2004/034894 A1 | 4/2004 |
| WO | WO 2007/120755 A2 | 10/2007 |
| WO | WO 2008/000403 A2 | 1/2008 |
| WO | WO 2008/144065 A1 | 11/2008 |
| WO | WO 2009/120349 A1 | 10/2009 |
| WO | WO 2010/097582 A1 | 9/2010 |

OTHER PUBLICATIONS

Notice of Allowance for U.S. Appl. No. 12/933,591, date mailed: Oct. 22, 2014, entitled "Ocular Imaging".
Office Action for U.S. Appl. No. 12/933,591, date mailed: May 21, 2014, entitled "Ocular Imaging".
Final Office Action dated Jun. 11, 2013 for U.S. Appl. No. 12/933,591, filed Jan. 4, 2011 entitled "System and Method for Detecting Amyloid Proteins".
Office Action dated Aug. 29, 2013 for U.S. Appl. No. 13/732,940, filed Jan. 2, 2013 entitled "Ocular Imaging".
"Notification Concerning Transmittal of International Preliminary Report on Patentability (Chapter I of the Patent Cooperation Treaty)" from International Application No. PCT/US2011/047628 mailed on Feb. 28, 2013.
Ansari, R.R., et al., "Measuring Lens Opacity: Combining Quasi-Elastic Light Scattering with Scheimpflug Imaging System," *Proceedings of SPIE*, 3246: 35-42 (1999).
Ansari, R.R. And Datiles, III, M. B., "Use of Dynamic Light Scattering and Scheimpflug Imaging for the Early Detection of Cataracts," *Diabetes Technology & Therapeutics*, 1(2): 159-169 (1999).
Chylack, L.T., et al., "Optiscan 2400, a New Clinical Instrument for Non-Invasive Measurement of Quasi-Elastic Light Scattering in Human Lens In Vivo," *Invest Opthalmol Vis Sci*, 46, E-Abstract 2911 (2002).
Dhenain, M., "Preclinical MRI and NMR Biomarkers of Alzheimer's Disease: Concepts and Applications," *Magnetic Resonance Insights*, 2: 75-91 (2008).
Goldstein, L.E., et al., "Cytosolic β-amyloid Deposition and Supranuclear Cataracts in Lenses from People with Alzheimer's Disease," *The Lancet*, 361: 1258-1265 (2003).
Patent Translate: Machine Translation to English for Description DE102007061987, consisting of 9 pages, dated Jul. 30, 2012.
Restriction Requirement issued in U.S. Appl. No. 11/786,514, entitled: "Ocular Imaging", dated Apr. 15, 2009.
Reply to Restriction Requirement issued in U.S. Appl. No. 11/786,514, entitled: "Ocular Imaging", dated Jun. 15, 2009.
Office Action issued in U.S. Appl. No. 11/786,514, entitled: "Ocular Imaging", dated Sep. 30, 2009.
Amendment filed in U.S. Appl. No. 11/786,514, entitled: "Ocular Imaging", dated Feb. 26, 2010.
Notice of Allowance issued in U.S. Appl. No. 11/786,514, entitled: "Ocular Imaging", dated Jul. 8, 2010.
Issue Fee paid in U.S. Appl. No. 11/786,514, entitled: "Ocular Imaging", dated Oct. 5, 2010.
Issue Notification issued in U.S. Appl. No. 11/786,514, entitled: "Ocular Imaging", dated Nov. 9, 2010.
Office Action issued in U.S. Appl. No. 12/897,432, entitled: "Ocular Imaging", dated Apr. 25, 2012.

(56) References Cited

OTHER PUBLICATIONS

Amendment filed in U.S. Appl. No. 12/897,432, entitled: "Ocular Imaging", dated Jul. 25, 2012.
Notice of Allowance issued in U.S. Appl. No. 12/897,432, entitled: "Ocular Imaging", dated Oct. 4, 2012.
Notification of Transmittal of the International Search Report and the Written Opinion, PCT/US2007/009009, dated Jul. 9, 2008.
Notification Concerning Transmittal of International Preliminary Report on Patentability, PCT/US2007/009009, dated Oct. 23, 2008.
Notification of Transmittal of the International Search Report and the Written Opinion of the International Search Authority, PCT/US2009/001885, dated Jun. 26, 2009.
International Preliminary Report on Patentability, PCT/US2009/001885, dated Sep. 28, 2010.
Office Action dated Jan. 31, 2013 for U.S. Appl. No. 12/933,591.
Jones-Bey, H., "Optical Technique May Diagnose Alzheimer's", *Laser Focus World*, 41(11): 1-2 (2005).
Hartung, P., "Optical Biosensors: Lasers Look Alzheimer's in the Eye", Laser Focus World, 42(10). Retrieved from the Internet on Oct. 26, 2011; URL: http://www.laserfocuswordl.com/articles/print/volume-42/issue- 10/features/optical-biosensors-lasers-look-alzheimersquos-in-the-eye.html. (2006).
Notification of Transmittal of the International Search Report and the Written Opinion of the International Searching Authority for PCT/US2011/047628; date of mailing Jan. 31, 2012.
Notice of Allowance for U.S. Appl. No. 13814,677, entitled: "System and Method for Detecting Amyloid Proteins", dated Aug. 26, 2015.
Office Action U.S. Appl. No. 13814,677, entitled: "System and Method for Detecting Amyloid Proteins", dated Mar. 6, 2015.

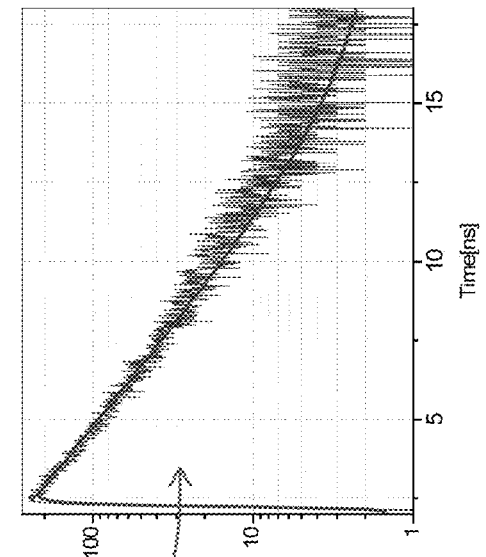
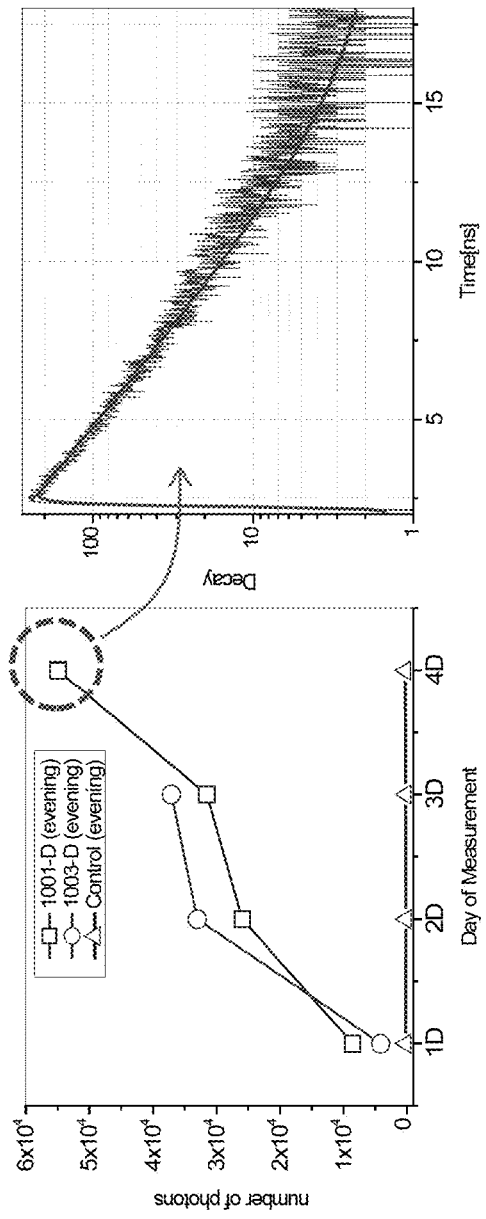
FIG. 9A
FIG. 9B

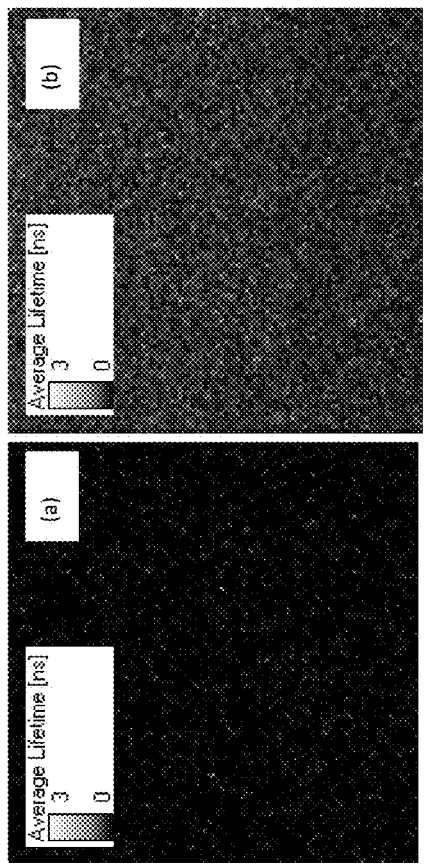
FIG. 11A
FIG. 11B
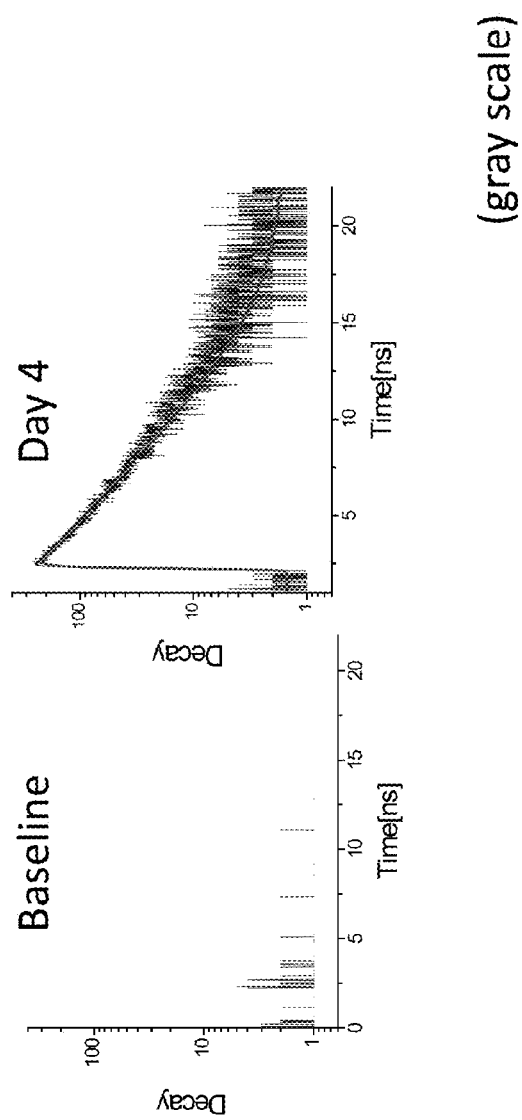
(gray scale)

SYSTEM AND METHOD FOR DETECTING AMYLOID PROTEINS

This application is a continuation of U.S. application Ser. No. 13/814,677, which is the U.S. National Stage Application of International Application No. PCT/US2011/047628, filed Aug. 12, 2011, which designates the U.S., published in English, and claims the benefit of prior U.S. Provisional Patent Application No. 61/374,131, filed Aug. 16, 2010 and U.S. Provisional Patent Application No. 61/425,490, filed Dec. 21, 2010; and claims priority under 35 U.S.C. §119 or 365 to European Patent Application No. 11001148.3, filed Feb. 11, 2011.

This application is also related to U.S. patent application Ser. No. 11/786,514, filed Apr. 11, 2007 now U.S. Pat. No. 7,828,436; and to U.S. patent application Ser. No. 12/154,226, filed May 21, 2008 and published as U.S. Patent Application Publication No. 2009/0041666; and U.S. Pat. No. 7,107,092 and U.S. Pat. No. 7,297,326.

The entire teachings of all of the above patents, publications and applications are incorporated herein by reference

BACKGROUND OF THE INVENTION

It is always desirable to detect diseases early in their progress. Early detection enables early treatment which has generally been proven to yield a higher success rate in treating various diseases. It has been discovered that analyzing peoples' eyes, and in particular the lenses of the eyes, can yield indications of various types of diseases. For example, researchers have found β-amyloid peptides and aggregates thereof in the supranucleus of the lens of the eyes of Alzheimer's disease [AD] victims. See U.S. Pat. No. 7,297,326 of Goldstein et al. Since the supranucleus is only a fraction of a millimeter thick, measurements obtained from this region of the crystalline lens need to be accurate in location, specific in information and fast in acquisition. This is especially true because the human eye is in almost constant motion even when a patient is fixating on an illuminated target.

It has been shown that the presence of, or an increase in, the amount of β-amyloid peptides and aggregates thereof in the supranuclear and/or cortical lens regions of a test mammal's eye compared to a normal control value indicates that the test mammal is suffering from, or is at risk of developing, a neurodegenerative disease such as an amyloidogenic disorder.

There is an ongoing need for systems and methods for permitting early detection of amyloidogenic disorders.

SUMMARY OF THE INVENTION

In accordance with an embodiment of the invention, there is provided a method for detecting in an eye of a mammal an amyloid protein, such as an amyloid protein comprising an aggregate. In some embodiments, detection of the amyloid protein is indicative of an amyloidogenic disorder. The method comprises illuminating the eye with a light source having at least one of a wavelength property, a polarization property or a combination thereof, each appropriate to produce fluorescence in at least an amyloid-binding compound when the amyloid-binding compound is bound to the amyloid protein, the amyloid-binding compound having been introduced to the eye and specifically binding to the amyloid protein indicative of the amyloidogenic disorder; receiving light including fluorescence produced as a result of the illuminating the eye; and determining a time decay rate of fluorescence for at least the fluorescence produced by the amyloid-binding compound bound to the amyloid protein, the determining permitting distinguishing of the presence of the amyloid-binding compound bound to the amyloid protein in the eye based on at least the time decay rate.

In further, related embodiments, the method may further comprise determining an intensity of fluorescence for at least the fluorescence produced by the amyloid-binding compound bound to the amyloid protein. A quantity of the amyloid-binding compound bound to the amyloid protein may be determined, based on at least one of the intensity and the time decay rate. The method may further comprise determining a location of an ocular interface such as a lens capsule of the eye based on an increase in a fluorescent signal due to natural fluorescence emitted from tissues of the eye. At least one region of the eye may be sampled using illumination by the light source, the sampling comprising performing at least one of a measure of the entire region or a sampling of different locations within the region or regions using illumination by the light source, the sampling of different locations comprising illuminating at least one point, plane and/or volume within the eye. The sampling may comprise sampling different locations across more than one region of the eye. For example, planar scans of the eye may be performed using the light source, in successive planes along a perpendicular axis extending depthwise into the eye. A location of a supranucleus of the eye may be determined based on (i) a distance away from a specific anatomical structure such as an interface of the lens capsule of the eye or corneal interface or (ii) a detection of a change (slope) in intensity measurement. The distinguishing the presence of the amyloid-binding compound bound to the amyloid protein may comprise distinguishing the amyloid-binding compound bound to the amyloid protein from background autofluorescence of eye tissues and autofluorescence of other non-specific particles as well as unbound imaging agent. The method may comprise distinguishing at least one of a presence and a quantity of more than one of the following: the amyloid-binding compound; the amyloid-binding compound bound to the amyloid protein; and the amyloid protein. The amyloid protein may comprise an aggregate or a pre-amyloid protein aggregate (including dimers, trimers or higher order oligomers of the peptides Aβ 1-42 and/or Aβ 1-40). For example, the amyloid protein may comprise beta-amyloid. The amyloidogenic disorder may comprise Alzheimer's disease.

In further, related embodiments, the amyloid-binding compound may comprise a molecular rotor, Chrysamine and/or a Chrysamine derivative, a Congo red and/or Congo red derivative amyloid-binding compound; a Chrysamine G or Chyrsamine G derivative amyloid-binding compound; a Thioflavin T or Thioflavin T derivative amyloid-binding compound; and a Thioflavin S or Thioflavin S derivative amyloid-binding compound. The method may comprise distinguishing at least the presence of the amyloid protein based only on detection of fluorescence. The method may further comprise determining the average number of photons with a specific decay rate in a certain area of the eye. A rate of delivery of the amyloid-binding compound to the eye, a spatial distribution of amyloid-binding compound delivered to the eye, and/or a gradient of concentration of the amyloid-binding compound at an interface of the cornea of the eye may be determined based on detected fluorescence. Further, a spatial distribution of the amyloid-binding compound and/or a temporal distribution of the amyloid-binding compound in the aqueous humor of the eye may be determined based on detected fluorescence.

The method may further comprise determining at least one dimension of an anatomical structure or substructure of the eye based on natural fluorescence excitation of at least a portion of the anatomical structure or substructure. Determining the at least one dimension may comprise at least one of determining a thickness of the structure or substructure, determining a shape of the structure or substructure, and determining a distance between one or more structure or substructures of the eye. For example, determining the at least one dimension may include determining a corneal thickness, corneal shape, aqueous humor depth, lens shape or lens thickness, or determining an internal measurement within the lens or other structure or substructure of the eye, such as a distance from the surface of the lens to the cortex or supranucleus or nucleus. The method may further comprise detecting fluorescence produced by the eye using a photodetector device, such as at least one of a photodiode, a photomultiplier, a charge-coupled device (CCD) and an intensified charge-coupled device (ICCD); for example a fast avalanche photodiode detector. The method may comprise performing a time correlation single photon counting of fluorescence produced by the eye. The time correlation single photon counting may comprise pulsing the light source and determining the time decay rate of fluorescence based on a distribution of photon counts as a function of time channel units.

In further, related embodiments, the method may comprise scanning within the eye to determine excited natural fluorescence and thereby to determine at least one region of interest in the eye; and sampling the at least one region of interest in the eye using illumination by the light source, the sampling comprising performing at least one of a measure of at least one entire region of the at least one region or a sampling of different locations within the at least one region using illumination by the light source, the sampling of different locations comprising illuminating at least one of a point, a plane or a volume within the at least one region; where the sampling is to determine an intensity of fluorescence and a time decay rate of fluorescence for at least the fluorescence produced by the amyloid-binding compound bound to the amyloid protein within the at least one sampled region. For example, the method may comprise performing an axial scan (z-scan) depthwise into the eye to determine excited natural fluorescence along each point of the axial scan and thereby to determine at least one location of interest in the eye; and performing planar scans of the eye using the light source, in successive planes perpendicular to the direction of the axial scan, to determine an intensity of fluorescence and a time decay rate of fluorescence for at least the fluorescence produced by the amyloid-binding compound bound to the amyloid protein at each point of each of the planar scans. The method may enable a real time search within the eye for the amyloid protein indicative of the amyloidogenic disorder.

In further, related embodiments, the method may further comprise illuminating the eye with light of an appropriate wavelength for a peak region of a fluorescent excitation spectrum for the amyloid-binding compound bound to the amyloid protein in the eye; and detecting light received from the eye of an appropriate wavelength for a peak region of a fluorescent emission spectrum for the amyloid-binding compound bound to the amyloid protein in the eye. The amyloid-binding compound may be Compound #11. The excitation spectrum may have a peak of about 470 nm, the illuminating of the eye being at a wavelength within plus or minus about 20 nm of the peak of the excitation spectrum, and the emission spectrum may have a peak of about 580 nm, the detecting of light received from the eye being at a wavelength within plus or minus about 20 nm of the peak of the emission spectrum.

In another embodiment according to the invention, there is provided a device for detecting an amyloid protein in an eye of a mammal. The device comprises a light source configured to emit light to illuminate the eye with at least one of a wavelength of light, a polarization of light or a combination thereof, each appropriate to produce fluorescence in at least an amyloid-binding compound when the amyloid-binding compound is bound to the amyloid protein, the amyloid-binding compound having been introduced to the eye and specifically binding to the amyloid protein indicative of the amyloidogenic disorder; and an optical unit configured to receive light including fluorescence produced as a result of the illumination of the eye and to determine a time decay rate of fluorescence for at least the fluorescence produced by the amyloid-binding compound bound to the amyloid protein, the determining permitting distinguishing of the presence of the amyloid-binding compound bound to the amyloid protein in the eye based at least on the time decay rate.

In further, related embodiments, the optical unit may be configured to determine the time decay rate for at least one of: a molecular rotor amyloid-binding compound; a Congo red or Congo red derivative amyloid-binding compound; a Chrysamine amyloid-binding compound; a Chrysamine derivative amyloid-binding compound; a Chrysamine G or Chyrsamine G derivative amyloid-binding compound; a Thioflavin T or Thioflavin T derivative amyloid-binding compound; and a Thioflavin S or Thioflavin S derivative amyloid-binding compound. The optical unit may determine an intensity of fluorescence for at least the fluorescence produced by the amyloid-binding compound bound to the amyloid protein. The optical unit may be configured to determine a quantity of the amyloid-binding compound bound to the amyloid protein, based on at least one of the intensity and the time decay rate. The optical unit may be configured to determine an average number of photons with a specific decay rate in a certain area of the eye. The light source may comprise a pulsed laser. The device may further comprise an optical scanning unit configured to scan light from the light source over locations in the eye. The optical scanning unit may comprise an objective lens mounted on a translation stage and a scanner comprising a galvanometric mirror. The optical scanning unit may be arranged to sample at least one region of the eye using illumination by the light source, the sampling comprising performing at least one of a measure of at least one entire region of the at least one region or a sampling of different locations within the at least one region using illumination by the light source, the sampling of different locations comprising illuminating at least one of a point, a plane or a volume within the at least one region. The optical scanning unit may be arranged to sample different locations across more than one region of the eye. In one example, the optical scanning unit may be arranged to perform planar scans of the eye using the light source, in successive planes along a perpendicular axis extending depthwise into the eye. The device may further comprise a photodetector unit for detecting fluorescence emitted from the eye, such as at least one of a photodiode, a photomultiplier, a charge-coupled device (CCD), and an intensified charge-coupled device (ICCD); for example an avalanche photodetector.

In further, related embodiments, the device may further comprise a time correlation single photon count module receiving electrical signals from the photodetector unit indicative of photon counts of fluoresced light from the eye. The device may comprise at least one processor module configured to determine the time decay rate of fluorescence based on a distribution of photon counts as a function of time channel units. The optical unit may be configured to distinguish the amyloid-binding compound bound to the amyloid protein from background autofluorescence of eye tissues and autofluorescence of other non-specific particles as well as unbound amyloid-binding compound. The optical unit may be configured to distinguish at least one of a presence and a quantity of more than one of the following: the amyloid-binding compound; the amyloid-binding compound bound to the amyloid protein; and the amyloid protein. The amyloid protein may comprise an aggregate or a pre-amyloid protein aggregate. For example, the amyloid protein may comprise beta-amyloid. The amyloidogenic disorder may comprise Alzheimer's disease.

In further, related embodiments, the optical unit may be configured to distinguish at least the presence of the amyloid protein based only on detection of fluorescence. The optical unit may be configured to determine a rate of delivery of the amyloid-binding compound to the eye, a spatial distribution of amyloid-binding compound delivered to the eye, and/or a gradient of concentration of the amyloid-binding compound at an interface of the cornea of the eye, based on detected fluorescence. The optical unit may be configured to determine at least one of a spatial distribution and a temporal distribution of the amyloid-binding compound in the aqueous humor of the eye based on detected fluorescence. The optical unit may be configured to determine a location of an ocular interface such as a lens capsule of the eye based on an increase in a fluorescent signal due to natural fluorescence emitted from tissues of the eye. The optical unit may be configured to determine a location of a supranucleus of the eye based on (i) a distance away from a specific anatomical structure such as an interface of the lens capsule of the eye or corneal interface or (ii) a detection of a change (slope) in intensity measurement. The optical unit may be configured to determine at least one dimension of an anatomical structure or substructure of the eye based on natural fluorescence excitation of at least a portion of the anatomical structure or substructure, where determining the at least one dimension may comprise at least one of determining a thickness of the structure or substructure, determining a shape of the structure or substructure, and determining a distance between one or more structure or substructures of the eye.

In further, related embodiments, the optical unit may be configured to scan within the eye to determine excited natural fluorescence and thereby to determine at least one region of interest in the eye; and to sample the at least one region of interest in the eye using illumination by the light source, the sampling comprising performing at least one of a measure of at least one entire region of the at least one region or a sampling of different locations within the at least one regions using illumination by the light source, the sampling of different locations comprising illuminating at least one of a point, a plane or a volume within the at least one region; where the sampling is to determine an intensity of fluorescence and a time decay rate of fluorescence for at least the fluorescence produced by the amyloid-binding compound bound to the amyloid protein within the at least one sampled region. For example, the optical unit may be configured to determine excited natural fluorescence along each point of an axial scan depthwise (z-scan) into the eye and thereby to determine at least one location of interest in the eye; and to determine an intensity of fluorescence and a time decay rate of fluorescence for at least the fluorescence produced by the amyloid-binding compound bound to the amyloid protein at each point of each of a set of planar scans (xy-scans) of the eye using the light source, in successive planes perpendicular to the direction of the z-scan. The device may be configured to enable a real time search within the eye for the amyloid protein indicative of the amyloidogenic disorder.

In further, related embodiments, the light source may be configured to emit light of an appropriate wavelength for a peak region of a fluorescent excitation spectrum for the amyloid-binding compound bound to the amyloid protein in the eye, and the optical unit may be configured to detect light of an appropriate wavelength for a peak region of a fluorescent emission spectrum for the amyloid-binding compound bound to the amyloid protein in the eye. The amyloid-binding compound may be Compound #11. The excitation spectrum may have a peak of about 470 nm, the light source being configured to emit light within plus or minus about 20 nm of the peak of the excitation spectrum, and the emission spectrum may have a peak of about 580 nm, the optical unit being configured to detect light within plus or minus about 20 nm of the peak of the emission spectrum. The amyloid protein may be indicative of an amyloidogenic disorder.

In another embodiment according to the invention, there is provided a method of diagnosing an amyloidogenic disorder or a predisposition thereto in a mammal, e.g., a primate (such as a human), canine, feline, ovine, bovine and the like. The method comprises illuminating an eye of the mammal with a light source having at least one of a wavelength property, a polarization property or a combination thereof, each appropriate to produce fluorescence in at least an amyloid-binding compound when the amyloid-binding compound is bound to an amyloid protein indicative of the amyloidogenic disorder, the amyloid-binding compound having been introduced to the eye and specifically binding to the amyloid protein indicative of the amyloidogenic disorder; receiving light including fluorescence produced as a result of the illuminating the eye; and determining a time decay rate of fluorescence for at least the fluorescence produced by the amyloid-binding compound bound to the amyloid protein, the determining permitting distinguishing of the presence of the amyloid-binding compound bound to the amyloid protein in the eye based on at least the time decay rate. An increase in binding of the amyloid-binding compound to the amyloid protein in the eye compared to a normal control level of binding indicates a diagnosis of an amyloidogenic disorder, or a risk of developing an amyloidogenic disorder in the mammal. The amyloidogenic disorder may be Alzheimer's disease.

In another embodiment according to the invention, there is provided a method for identifying an anatomical structure of an eye of a mammal. The method comprises illuminating the eye with a light source having at least one of a wavelength property, a polarization property or a combination thereof, each appropriate to produce natural fluorescence in the anatomical structure of the eye; and determining a location within the eye of greatest change in intensity of the natural fluorescence produced by the illuminating with the light source, the determining permitting identifying of the anatomical structure based on the location of greatest change in intensity of the natural fluorescence. In a particular embodiment, a device described herein in accordance with an embodiment of the invention is used in such a method.

In further, related embodiments, the anatomical structure may comprise an anatomical structure of the anterior segment of the eye. The identifying of the anatomical structure may comprise determining the location of an anatomical interface, such as determining the location of an interface of the lens capsule of the eye based on determining a location of the greatest increase in intensity of the natural fluorescence. The identifying of the anatomical structure may comprise determining at least one of a corneal thickness, corneal shape, aqueous humor depth, lens shape, lens thickness, and thickness and/or shape of substructures of the lens (e.g., lens capsule, cortex, supranucleus, nucleus) of the eye based on natural fluorescence produced by the light source in the eye; and may comprise determining an intra-ocular distance between at least two anatomical structures of the eye. The method may further comprise using the light source to detect in the eye of the mammal an amyloid protein indicative of an amyloidogenic disorder. The method may comprise illuminating the eye of the mammal with the light source, the light source further comprising at least one of a wavelength property, a polarization property or a combination thereof, each appropriate to produce fluorescence in at least an amyloid-binding compound when the amyloid-binding compound is bound to the amyloid protein indicative of the amyloidogenic disorder, the amyloid-binding compound having been introduced to the eye and specifically binding to the amyloid protein indicative of the amyloidogenic disorder; receiving light including fluorescence produced as a result of the illuminating the eye; and determining a time decay rate of fluorescence for at least the fluorescence produced by the amyloid-binding compound bound to the amyloid protein, the determining permitting distinguishing of the presence of the amyloid-binding compound bound to the amyloid protein in the eye based on at least the time decay rate. The distinguishing the presence of the amyloid-binding compound bound to the amyloid protein may comprise distinguishing the amyloid-binding compound bound to the amyloid protein from background autofluorescence of eye tissues and autofluorescence of other non-specific particles as well as unbound amyloid-binding compound. The method may enable a real time search within the eye for the amyloid protein indicative of the amyloidogenic disorder. The method may further comprise illuminating the eye with light of an appropriate wavelength for a peak region of a fluorescent excitation spectrum for the amyloid-binding compound bound to the amyloid protein in the eye; and detecting light received from the eye of an appropriate wavelength for a peak region of a fluorescent emission spectrum for the amyloid-binding compound bound to the amyloid protein in the eye. The amyloid-binding compound may be Compound #11. The excitation spectrum may have a peak of about 470 nm, the illuminating of the eye being at a wavelength within plus or minus about 20 nm of the peak of the excitation spectrum, and the emission spectrum may have a peak of about 580 nm, the detecting of light received from the eye being at a wavelength within plus or minus about 20 nm of the peak of the emission spectrum In further, related embodiments, a method may permit distinguishing between at least two different fluorophores with similar fluorescence spectra in an eye based on at least the time decay rate, the similar fluorescence spectra comprising at least one of a significant overlap in emission spectra and excitation spectra. A method may further comprise representing a distribution of at least one of a fluorescent intensity and a lifetime decay of at least one fluorophore in two dimensions. Further, a method may comprise determining a number of photons bound and a number of photons unbound in an eye based on at least one of a fluorescent intensity and a lifetime decay of at least one fluorophore. A method may comprise representing in two dimensions a distribution of fluorescent intensity and lifetime decay of bound amyloid-binding compound to protein and unbound amyloid-binding compound to protein. The representing in two dimensions may be synchronized with at least one of a scanner and a laser. The method may further comprise determining a parameter by averaging a fluorescent intensity, associated with a specific lifetime decay, over a specific area of the eye. In addition, the method may further comprise aligning an alignment light source with the eye along a confocal path to determine a reference point within the eye.

In a further embodiment according to the invention, there is provided a method for determining bound fluorophores on a protein in an ocular tissue. The method comprises illuminating the ocular tissue with a light source having at least one of a wavelength property, a polarization property or a combination thereof, each appropriate to produce fluorescence in at least an amyloid-binding compound when the amyloid-binding compound is bound to the protein, the amyloid-binding compound having been introduced to the ocular tissue and specifically binding to the protein; receiving light including fluorescence produced as a result of the illuminating the eye; and determining a time decay rate of fluorescence for at least the fluorescence produced by the amyloid-binding compound bound to the protein, the determining permitting distinguishing of the presence of the amyloid-binding compound bound to the protein in the ocular tissue based on at least the time decay rate.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 9A is a plot of the frequency of photons of a specific decay rate pertaining to the fluorescent amyloid-binding Compound #11 measured in rabbits in an in vivo study, in accordance with an embodiment of the invention.

FIG. 9B is a fluorescence histogram corresponding to the study of FIG. 9A, in accordance with an embodiment of the invention.

FIGS. 11A and 11B are two fluorescence lifetime images taken at baseline and after the end of the fourth day of an animal study, in an experiment in accordance with an embodiment of the invention.

DETAILED DESCRIPTION OF THE INVENTION

Figure 1:
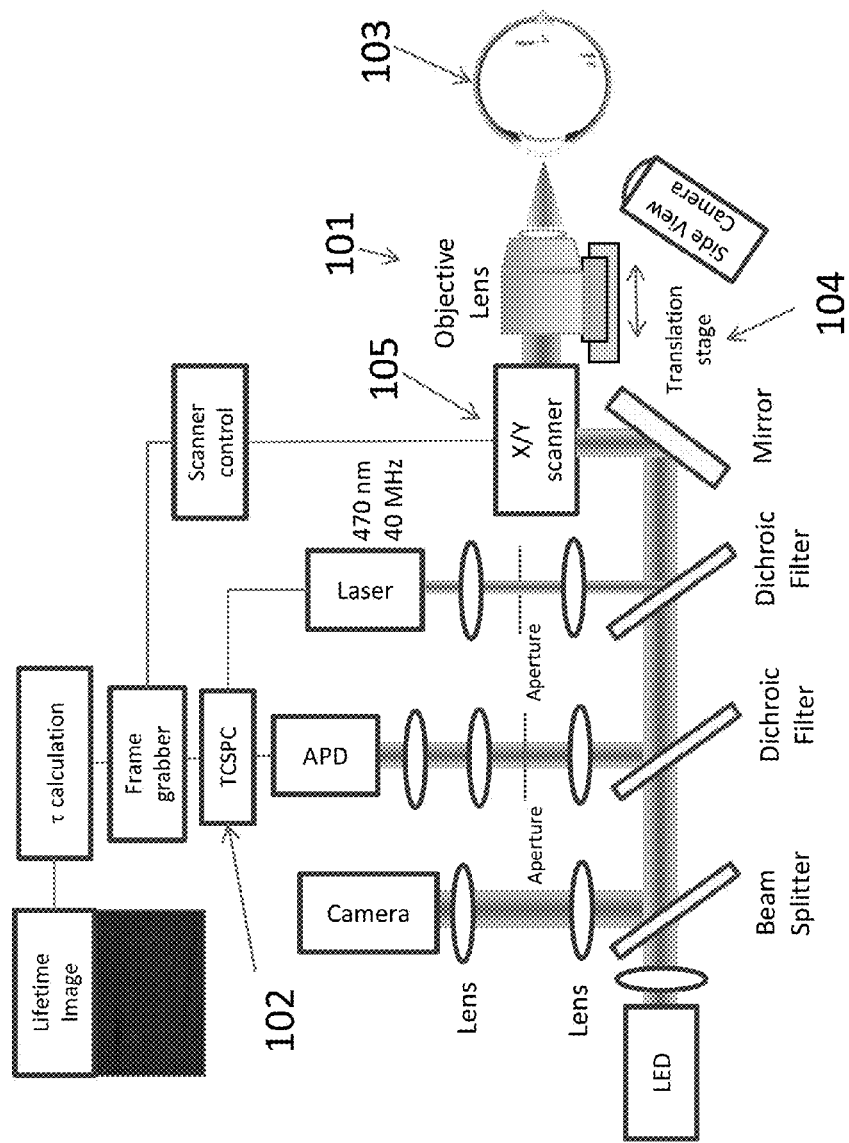
FIG. 1 is a schematic diagram of an optical system in accordance with an embodiment of the invention.

A description of example embodiments of the invention follows.

In accordance with an embodiment of the invention, there is provided a system and method for non-invasive, early and reliable detection of an amyloid protein, which may form, or have formed, into an aggregate. In some embodiments, detection of the amyloid protein and/or aggregate is indicative of an amyloidogenic disorder. Amyloidogenic disorders include AD, Familial AD, Sporadic AD, Creutzfeld-Jakob disease, variant Creutzfeld-Jakob disease, spongiform encephalopathies, Prion diseases (including scrapie, bovine spongiform encephalopathy, and other veterinary prionopathies), Parkinson's disease, Huntington's disease (and trinucleotide repeat diseases), amyotrophic lateral sclerosis, Down's Syndrome (Trisomy 21), Pick's Disease (Frontotemporal Dementia), Lewy Body Disease, neurodegeneration with brain iron accumulation (Hallervorden-Spatz Disease), synucleinopathies (including Parkinson's disease, multiple system atrophy, dementia with Lewy Bodies, and others), neuronal intranuclear inclusion disease, tauopathies (including progressive supranuclear palsy, Pick's disease, corticobasal degeneration, hereditary frontotemporal dementia (with or without Parkinsonism), a pre-morbid neurodegenerative state and Guam amyotrophic lateral sclerosis/parkinsonism dementia complex). These disorders may occur alone or in various combinations. Amyloid protein analysis is also useful to detect Transmissible Spongiform Encephalopathies (TSEs), which are prion-mediated diseases characterized by fatal spongiform neurodegeneration of the brain and are associated with severe and fatal neurological signs and symptoms. TSE prionopathies include Creutzfeld-Jacob Disease (CJD); new variant, Creutzfeld-Jacob Disease (nv-CJD); Gertsmann-Straussler-Scheinker syndrome; fatal familial insomnia; Kuru; Alpers Syndrome; Bovine Spongiform Encephalopathy (BSE); scrapie; and chronic wasting disease (CWD).

The diagnostic methods may be carried out for ocular tissues of mammals, for example a primate (such as a human), canine, feline, ovine, bovine and the like. Individuals (e.g., human subjects) to be tested include those suspected of suffering from such disorders (patients) or who are at risk of developing such disorders. For example, individuals with a family history of AD or other risk factors such as advanced age are tested using the techniques described herein. Persons who are not known to be suffering or at risk of developing such disorders may also be tested.

The diagnostic methods are carried out by contacting an ocular tissue of a mammal (e.g., a human subject) with a fluorophore compound that binds to an amyloid protein, e.g., β-amyloid (Aβ). By "amyloid protein," it is meant a protein or peptide that is associated with an AD neuritic senile plaque, regardless of whether the amyloid protein is aggregated (fully or partially). Preferably, the amyloid protein is amyloid precursor protein (APP) or an (e.g., naturally-occurring) proteolytic cleavage product of APP such as Aβ. APP cleavage products include Aβ1-40, Aβ2-40, Aβ1-42, as well as oxidized or crosslinked Aβ. The fluorophore compounds may also bind to naturally-occurring variants of APP and Aβ, including single nucleotide polymorphic (SNP) variants. The fluorophore compounds may, but need not necessarily, bind to β-amyloid aggregate. A discussion of fluorophore binding to β-amyloid aggregates may be found in Goldstein et al., "Cytosolic β-amyloid deposition and supranuclear cataracts in lenses from people with Alzheimer's disease," Lancet 2003; 361: 1258-65, the entire disclosure of which is hereby incorporated herein by reference.

Aggregates containing Aβ, the pathogenic protein which accumulates in AD, have been found to form supranuclear/deep cortical cataracts within the lenses as well as in the brains of Alzheimer's disease patients. Aβ deposits collect as intracellular aggregates within the cytosol of lens cortical fiber cells. It has been shown that lens Aβ exists as soluble apparent monomeric and dimeric species within the adult human lens at levels comparable to those in normal adult brain. A substantial proportion of lens Aβ is bound to other lens proteins, including the abundant lens structural protein αB-crystallin. Aβ and αB-crystallin exhibited nanomolar intermolecular binding affinity in vitro and co-immunoprecipitated from formic acid-treated human lens homogenates, indicating strong protein-protein association. Human Aβ1-42 promotes lens protein aggregation with increased β-sheet content. Aβ-potentiated lens protein aggregation was blocked by metal chelation or reactive oxygen species scavengers, thus demonstrating that metalloprotein redox reactions are involved in this lens protein aggregation process and supranuclear cataract formation in AD.

The data indicate that a pathologic interaction between Aβ and lens proteins occurs. Furthermore, these Aβ-mediated reactions in the lens indicate that amyloidogenic Aβ species, particularly the human Aβ1-42 species which is prominently involved in AD pathophysiology, were potent pro-oxidant peptides which fostered lens protein aggregation and supranuclear/cortical cataract formation. Further information regarding protein aggregation and cataract formation may be found in U.S. Pat. No. 7,107,092 of Goldstein et al., the entire teachings of which are hereby incorporated herein by reference.

In accordance with an embodiment of the invention, an increase in binding of the fluorophore compound to an ocular tissue, e.g., an intracellular compartment of a lens cell, compared to a normal control level of binding indicates that the mammal is suffering from or is at risk of developing AD. As used herein, a "fluorophore" or "fluorophore compound" is any substance having desirable fluorescent characteristics when illuminated with light of a certain wavelength and/or polarization property. Preferably, in techniques discussed herein, the fluorophore is an "amyloid-binding compound," which as used herein means a compound that binds to an amyloid protein, where "amyloid protein" is as defined above. Such a fluorophore may be an amyloid-binding compound that naturally fluoresces when exposed to light of a certain wavelength and/or polarization property. Alternatively or in addition, the fluorophore may be a compound that includes a fluorescent tag portion in combination with an amyloid-binding compound portion, where the amyloid-binding compound portion would generally not exhibit the desired fluorescence characteristics in the absence of the fluorescent tag. In one embodiment, the fluorophore has the following properties: exhibits good solubility in any medium in which the fluorophore is used; penetrates the cornea of the eye; and binds to amyloid protein. The fluorophore may have different fluorescent characteristics when bound to amyloid and when unbound. For example, the spectral intensity and time decay rate of fluorescence of the fluorophore may change when the fluorophore is bound to amyloid as compared to when it is unbound. Compound #11 (discussed further below in connection with FIG. 5) is such a fluorophore, in which the time decay rate changes when the compound is bound to amyloid as compared to when it is unbound. Further discussion of such properties of fluorophores, in particular Compound #11, may be found in J. Sutharsan et al., "Rational Design of Amyloid Binding Agents Based on the Molecular Rotor Motif," Chem Med Chem 2010, 5, 56-60, the entire disclosure of which is hereby incorporated herein by reference. Preferably, the fluorophore compound binds to $A\beta$1-42 or another fragment of an amyloid precursor protein (APP). The fluorophore compounds may preferentially bind to amyloid proteins compared to other $\beta$-pleated sheet containing proteins. As noted above, the fluorophore compound may contain a fluorescent probe or may act as a fluorophore without the addition of a fluorescent probe. For example, the fluorescent probe or fluorophore may be a Chrysamine or Chrysamine derivative compound such as {(trans, trans), -1-bromo-2,5-bis-(3-hydroxycarbonyl-4-hydroxy)styrlbenzene (BSB)}. In a particular embodiment, the fluorophore may be Compound #11 (discussed further below in connection with FIG. 5), which is a fluorescent compound designed according to the molecular rotor motif. In accordance with an embodiment of the invention, the amyloid-binding compound may be a molecular rotor, Chrysamine and/or a Chrysamine derivative. Exemplary fluorophores are discussed in U.S. Pat. No. 6,849,249 (herein incorporated by reference in its entirety), and include Chrysamine or Chrysamine derivative compounds such as {(trans, trans), -1-bromo-2,5-bis-(3-hydroxycarbonyl-4-hydroxy) styrlbenzene (BSB)}. Chrysamine G and derivatives thereof are known in the art (e.g., U.S. Pat. Nos. 6,133,259; 6,168,776; 6,114,175). These compounds bind to $A\beta$ peptides, but are not fluorescent. The diagnostic methods may utilize a fluorescent amyloid-binding Chrysamine G derivative to detect $A\beta$ peptides in the eye. Bioavailable fluorescent probes may also be used. Such fluorophores and probes are commercially-available, e.g, from Molecular Probes, Inc., Eugene, Oreg., U.S.A. Some dyes, e.g., X-34 or {(trans, trans), -1-bromo-2,5-bis-(3-hydroxycarbonyl-4-hydroxy) styrlbenzene (BSB)} (Styren et al., 2000, J. Histochem. 48:1223-1232; Link et al., 2001, Neurobiol. Aging 22:217-226; and Skrovonsksy et al., 2000, Proc. Natl. Acad. Sci. U.S.A. 97:7609-7614) have been used to analyze brain tissue (but not eye tissue). These probes emit light in the blue-green range, thus the level of fluorescence, which is diagnostically relevant, exceeds the amount of human lens autofluorescence in the blue-green range. Other useful compounds include a detectable methoxy agent such as Me-X04 (1,4-bis(4'-hydroxystyrl)-2-methoxybenzene). Other methoxy agents include, e.g., Chrysamine or Chrysamine derivative compounds such as {(trans, trans), -1-bromo-2,5-bis-(3-hydroxycarbonyl-4-hydroxy) styrlbenzene (BSB)}. Such compounds are described in Mathis et al., Curr. Pharm. Des., vol. 10(13):1469-93 (2004); U.S. Pat. Nos. 6,417,178; 6,168,776; 6,133,259; and 6,114,175, each of which is hereby incorporated by reference in its entirety. Other amyloid-binding probes such as thioflavin T, thioflavin S, Congo red dye, derivatives of the foregoing, or other derivatives may also be used. Further information regarding detectably-labeled compounds may be found in U.S. Pat. No. 7,297,326 of Goldstein et al., the entire teachings of which are hereby incorporated herein by reference. In addition, further information regarding the foregoing may be found in U.S. Patent Application Publication No. 2008/0088795, U.S. Patent Application Publication No. 2009/0041666, and U.S. Pat. No. 7,107,092, the entire teachings of which applications and patents are hereby incorporated herein by reference. In a particular embodiment, the fluorophore may be Compound #11 (discussed further below in connection with FIG. 5).

Further information regarding related methods, amyloidogenic disorders, amyloid proteins and fluorophore compounds may be found in U.S. Pat. No. 7,297,326 of Goldstein et al., U.S. Pat. No. 7,107,092 of Goldstein et al., and U.S. Pat. No. 6,849,249 of Goldstein et al., the entire teachings of all of which patents are hereby incorporated herein by reference. In addition, further information regarding the foregoing may be found in U.S. Patent Application Publication No. 2008/0088795, U.S. Patent Application Publication No. 2009/0041666, the entire teachings of which applications are hereby incorporated herein by reference.

The methods provided herein can further comprise comparing the test patient lens fluorescence after fluorophore administration to a suitable control. Examples of a suitable control include the endogenous autofluorescence of a non-AD subject (or population of individuals) or to the level of fluorescence of a non-AD subject (or population of non-AD subjects) after fluorophore administration.

In accordance with an embodiment of the invention, a quantity of amyloid protein found to be present in the eye based on techniques disclosed herein, may be compared with statistical analyses that indicate the quantity of amyloid protein that signifies a disease condition, or the risk of developing a disease condition. Without wishing to be bound by theory, it is believed that healthy adults typically have at least some minimal level of amyloid protein in the supranucleus region of the lens of the eye. Techniques disclosed herein may therefore be used to determine whether an individual has a quantity of amyloid protein in the eye that is a statistically significant level above a normal, control level of amyloid protein in the eye. A study of amyloid protein deposition in the eyes of persons with Alzheimer's disease may be found in Goldstein et al., "Cytosolic $\beta$-amyloid deposition and supranuclear cataracts in lenses from people with Alzheimer's disease," Lancet 2003; 361: 1258-65, the entire disclosure of which is hereby incorporated herein by reference.

As discussed further below in connection with Experiment #1, an embodiment according to the invention has been shown to be able to distinguish between amyloid-binding compound when bound to amyloid protein, as opposed to unbound amyloid-binding compound. In particular, results in Experiment #1 have found a time decay rate of, for example, 1.4 nsec for the unbound fluorescent amyloid-binding compound—here, Compound #11; and a time decay rate of, for example, 2.25 nsec for the amyloid-binding compound when bound to amyloid protein—here, aggregated beta-amyloid (Aβ) peptide. In accordance with an embodiment of the invention, the detection of unbound amyloid-binding compound Compound #11 may be indicated by time decay rates of 1.4 nsec plus or minus 0.3 nsec, whereas the detection of bound amyloid-binding compound Compound #11 bound to amyloid protein may be indicated by time decay rates of 2.25 nsec plus or minus 0.3 nsec. Other decay rates and confidence levels for distinguishing amyloid-binding compound from amyloid protein may be used.

In accordance with an embodiment of the invention, there is provided a fluorescence imaging method and device for detection of amyloid-binding compound-tagged beta-amyloid (Aβ) proteins in the lens of the eye, and uses thereof. In one aspect, a device provided herein is an optical imaging device that employs a fluorescence scanning mechanism combined with lifetime spectroscopy to enable the detection of fluorescent molecules and to provide information on their spatial distribution, as well on the nature of their surroundings.

In accordance with an embodiment of the invention, the device, e.g., a multi-functional optical scanning fluorescent system, enables the identification of the anatomical structures of the anterior segments of the eye based on their natural fluorescence excitation; and can provide spatial information on the anterior segments of the eye, such as corneal thickness and lens shape, and can provide intraocular distances.

In addition, a multi-functional optical scanning system in accordance with an embodiment of the invention provides an in vivo ocular pharmacokinetics investigation tool for exogenous fluorescent amyloid-binding compounds in the eye, without being bound to amyloid protein. For example, the system can determine the gradient concentration of amyloid-binding compounds at the corneal interfaces, such as the tear film/corneal epithelial interface. Further, the system can determine spatial and temporal information regarding the bioavailability of amyloid-binding compounds in the aqueous humor.

Further, a multi-functional optical scanning system in accordance with an embodiment of the invention permits detection of fluorescent molecules and differentiation between them based on their optical signatures, such as fluorescence decay time (τ). The system permits detection of tagged fluorescent amyloid-binding compound bound to Aβ in the lens of the eye; detection of natural fluorescence in the eye; and discrimination between (i) tagged fluorescent amyloid-binding compound bound to Aβ in the lens of the eye and (ii) natural fluorescence in the eye. As used herein, "natural fluorescence" signifies natural fluorescence in the eye that can occur independently of an introduced imaging agent.

FIG. 1 is a schematic diagram of an optical device in accordance with an embodiment of the invention. Fluorescence excitation is achieved by a pulsed laser beam that is focused by a high numerical aperture objective lens 101 into the eye. Fluorescence is detected using a time correlation single photon counting (TCSPC) technique through a confocal configuration with a fast avalanche photodiode detector (APD) 102. TCSPC is performed by using a short pulse of light to excite the sample (eye) 103 repetitively, and recording the subsequent fluorescence emission as a function of time. This usually occurs on the nanosecond timescale.

In the embodiment of FIG. 1, identification of the anatomical structures of the lens is performed by scanning the objective lens 101 on axis using a translation stage 104. The signal is measured at every point along the scan in order to reveal the anatomical structures of the anterior segments such as the cornea, lens capsule and supranucleus region of the lens. In addition, the scan provides information about the pharmaco-kinetics of exogenous amyloid-binding compounds applied to the eye. Such information provides not only spatial and temporal information of the amyloid-binding compound, but also the concentration of the amyloid-binding compound that penetrates through the cornea and into the aqueous humor.

In the embodiment of FIG. 1, once the location of interest in the eye is known from the excited natural fluorescence measured at every point along the axial scan, another scan is executed in a plane (xy) perpendicular to the optical axis using a set of galvanometer mirrors 105. To ensure allocation of the measured fluorescence decay curves to the corresponding site of the two-dimensional scanning, the galvanometer set scanning is synchronized with the laser pulses and photodetection for time-correlated individual photon counting. Such an xy-scan reveals an image with fluorescence decay time information for each site (pixel). In the embodiment of FIG. 1, one or more modules may be implemented using dedicated, specialized hardware modules and/or using a general purpose computer specially-programmed to perform the modules' functionality, including, for example, the Frame Grabber module, TCSPC module, τ Calculation module and scanner control module. A general purpose computer and/or one or more specialized hardware modules may receive data from each other via data cables and data ports appropriate for the modules' functionality.

In the embodiment of FIG. 1, for time-correlated individual photon counting, the decay curve of the autofluorescence is registered for each scanned location of the lens and thus a two-dimensional representation of the fluorophores' distributions can be evaluated and analyzed based on their fluorescence decay time as well as on their intensity. The image of the calculated decay times can be encoded by false colors and can be superimposed on the intensity image for better clinical interpretation. Since the fluorescence decay time is a characteristic for each fluorescence molecule, one can determine and separate the fluorophores (amyloid-binding compound from natural fluorescence of the lens) being excited in the sample volume. By combining fluorescence intensity and lifetime measurements, an extra dimension of information is obtained to discriminate among several fluorescent labels.

As discussed herein, a device in accordance with an embodiment of the invention may comprise a light source. As used herein a "light source" may be any light source that can be configured to emit light to illuminate the eye with at least one of a wavelength and a polarization of light appropriate to produce fluorescence in at least an amyloid-binding compound when the amyloid-binding compound is bound to the amyloid protein, in a fashion such that the time decay rate of fluorescence may subsequently be determined based on the fluorescence that is received as a result of the illumination.

Figure 12:
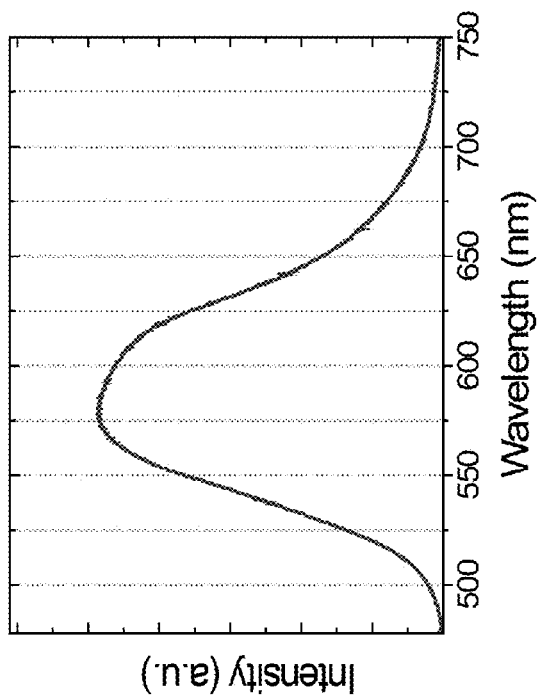
FIG. 12 is an emission spectrum of the fluorescent amyloid-binding compound Compound #11 when excited at 470 nm, in accordance with an embodiment of the invention.

In an embodiment according to the invention, the light source may be configured to emit light of an appropriate wavelength for a peak region of a fluorescent excitation spectrum for the amyloid-binding compound bound to the amyloid protein in the eye, and the optical unit may be configured to detect light of an appropriate wavelength for a peak region of a fluorescent emission spectrum for the amyloid-binding compound bound to the amyloid protein in the eye. For example, where the amyloid-binding compound is Compound #11, the excitation spectrum has a peak of about 470 nm, and the light source may be configured to emit light within plus or minus about 20 nm of the peak of about 470 nm, such as within plus or minus 5 nm, plus or minus 10 nm, plus or minus 15 nm or plus or minus 20 nm of 470 nm. Further, the emission spectrum for Compound #11 has a peak of about 580 nm, and the optical unit may be configured to detect light within plus or minus about 20 nm of the peak of about 580 nm, such as within plus or minus 5 nm, plus or minus 10 nm, plus or minus 15 nm or plus or minus 20 nm of 580 nm. In general, there is typically a shift between the peak of the excitation spectrum and the peak of the emission spectrum of a fluorescent compound. In accordance with an embodiment of the invention, it is useful to use a compound in which the peak of the emission spectrum is significantly shifted relative to the excitation spectrum, in order to enable the distinguishing of fluorescence from the bound fluorophore from natural autofluorescence of the eye. For example, an emission spectrum having a peak greater than about 500 nm is advantageous for distinguishing from the natural autofluorescence of the eye. Compound #11 proves useful for such a purpose, having an emission spectrum with a peak of about 580 nm, shifted significantly from the excitation spectrum with a peak of about 470 nm. FIG. 12 is an emission spectrum of the fluorescent amyloid-binding compound Compound #11 when excited at 470 nm, in accordance with an embodiment of the invention. Other excitation and emission spectra that may be used will be apparent to those of skill in the art based on the foregoing.

In accordance with an embodiment of the invention, the device may use an "optical unit," which as used herein means any unit that can be configured to receive light including fluorescence produced as a result of the illumination of the eye and to determine a time decay rate of fluorescence for at least the fluorescence produced by the amyloid-binding compound bound to the amyloid protein, the determining permitting distinguishing of the presence of the amyloid-binding compound bound to the amyloid protein in the eye based at least on the time decay rate. For example, with reference to FIG. 1, the optical unit may include one or more of the objective lens 101, translation stage 104, scanner 105, photodetector 102, a camera, an LED, the various lenses, apertures, beam splitters, dichroic filters, the time decay calculation module, the frame grabber module, the TCSPC module, and the scanner control module. Portions of the functionality of the optical unit may be implemented by a specially-programmed general purpose computer, or by dedicated hardware, for example for performing time decay calculations.

In accordance with an embodiment of the invention, the functionality of the objective lens 101, translation stage 104 and scanner with galvanometer mirrors 105 may be performed using a variety of different possible devices, instead of or in addition to those components. Collectively, the functionality of the translation stage, objective lens and scanner with galvanometric mirrors are referred to herein as being implemented by an "optical scanning unit," which may refer to any device or collection of devices that perform the equivalent function of scanning a light beam over desired regions of interest in the eye, including for the purpose of determining reference points within the eye and for the purpose of analyzing fluorophores within the eye. Such an optical scanning unit may perform the functions of inducing translation motion of a lens, or motion of lens along a multi-dimensional path of motion; and may perform the functions of scanning the light over regions of interest, for example performing a point, planar, volumetric or other type of scan of the light beam over regions of interest, for example by inducing motion in a mirror or other optical device in the optical path of a light beam.

In the embodiment of FIG. 1, the use of a confocal arrangement means that a dilation agent need not be used, as may be required in systems in which light needs to enter the eye off-axis, for example, at a 45-degree angle. This is of convenience to patients.

Figure 2:
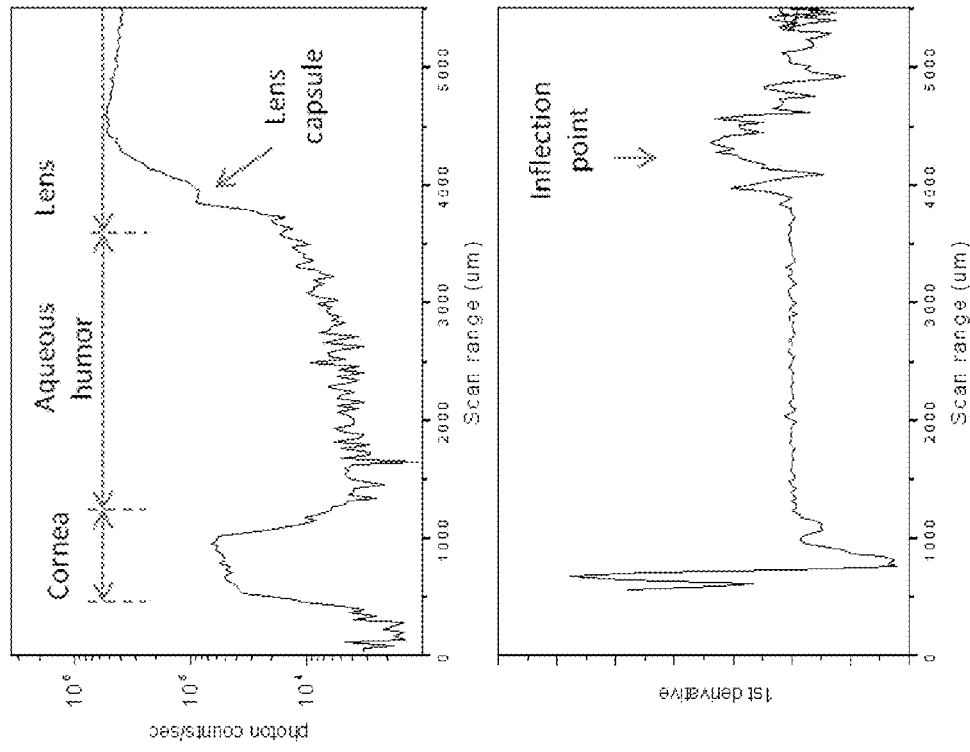
FIG. 2A is a graph of fluorescence intensity versus displacement, measured during performance of an algorithm for detecting a lens interface in a z-scan of the eye.
FIG. 2B is a graph of the first derivative of the graph of FIG. 2A, in accordance with an embodiment of the invention.

FIG. 2A is a graph of natural fluorescence intensity versus displacement, measured during performance of an algorithm for detecting a lens interface in a scan along the illumination path (z-scan) of the eye, and FIG. 2B is a graph of the first derivative of the graph of FIG. 2A, in accordance with an embodiment of the invention. The rationale for the algorithm is the assumption that the location where the natural fluorescence intensity value increase is the greatest per unit scan distance is a reasonable indicator of where the lens boundary begins. In particular, the algorithm determines the distance from the z-scan start point that corresponds to the maximum inflection point in the fluorescence intensity. In one embodiment, the algorithm proceeds as follows, and may run in real time:

1) Gather data in a two dimensional array where the first (independent variable) dimension is distance from start point, i.e., scan distance, as measured via rotary encoder, and the second dimension (dependent variable) is fluorescence intensity as measured via photon detector (APD).

2) Convolve the data array with a five point moving average profile to smooth the intensity values, i.e., remove high frequency noise that interferes with differentiation.

3) Convolve the smoothed data array with differential profile to obtain the first derivative of the intensity array.

4) Search the intensity first derivative array for maximum differential intensity value. This is the maximum inflection point. Determine the corresponding scan distance.

As shown in FIGS. 2A and 2B, a location of the lens capsule may be determined using the above technique. Further, the locations of, and distances between, anatomical structures such as the cornea, aqueous humor and lens may also be determined. An offset may be applied to specify a distance of a measurement from a specific datum along any axis.

Figure 3:
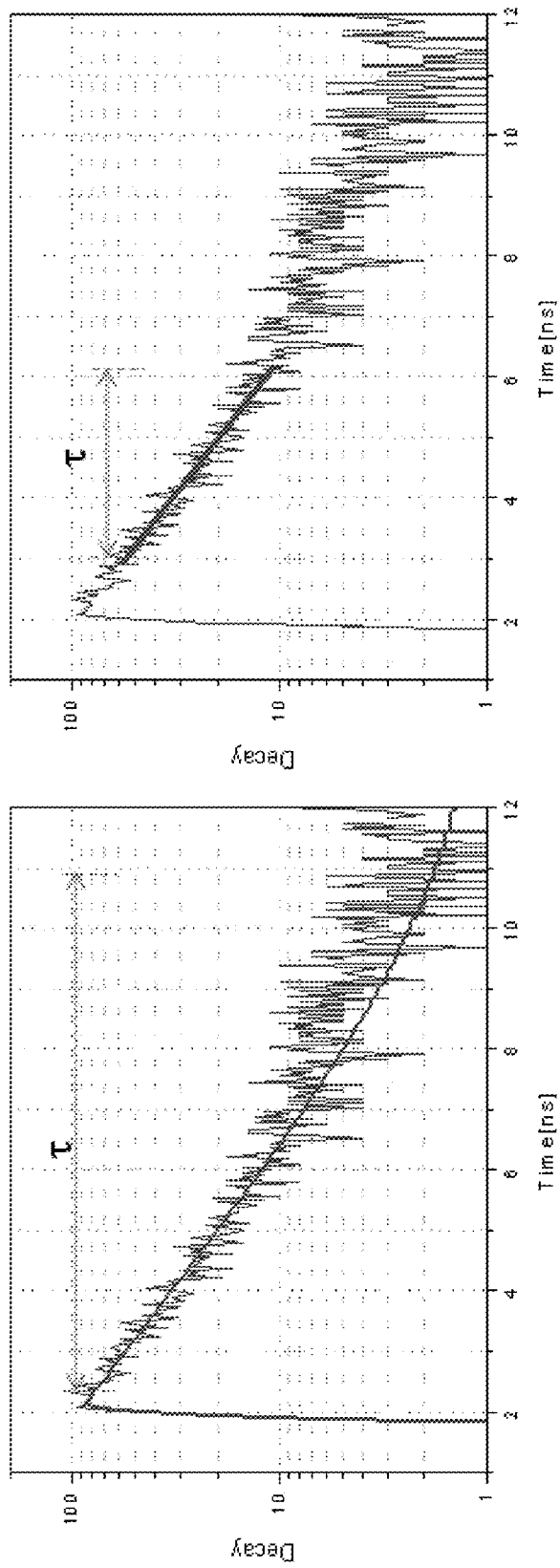
FIGS. 3A and 3B are graphs illustrating determination of fluorescence decay time in accordance with an embodiment of the invention.

FIGS. 3A and 3B are graphs illustrating determination of fluorescence decay time in accordance with an embodiment of the invention. Fluorescence decay time may be calculated by a single or double fit exponential (FIG. 3A) to a curve of intensity (here, in photons/sec), versus time (here, in nanoseconds). It can be also obtained by a linear fit to the slope (FIG. 3B). As used herein, a "time decay rate of fluorescence" signifies a characteristic time constant of a decay curve of fluorescence intensity; for example, an exponential time constant or a slope fitted to the fluorescence decay curve.

The above algorithms of FIGS. 2A, 2B and 3A, 3B may, for example, be implemented using dedicated, specialized hardware modules and/or using a general purpose computer specially-programmed to perform the above algorithms. Such modules may, for example, use or receive data from the TCSPC module, Frame Grabber module, τ-calculation module of the embodiment of FIG. 1.

Figure 4:
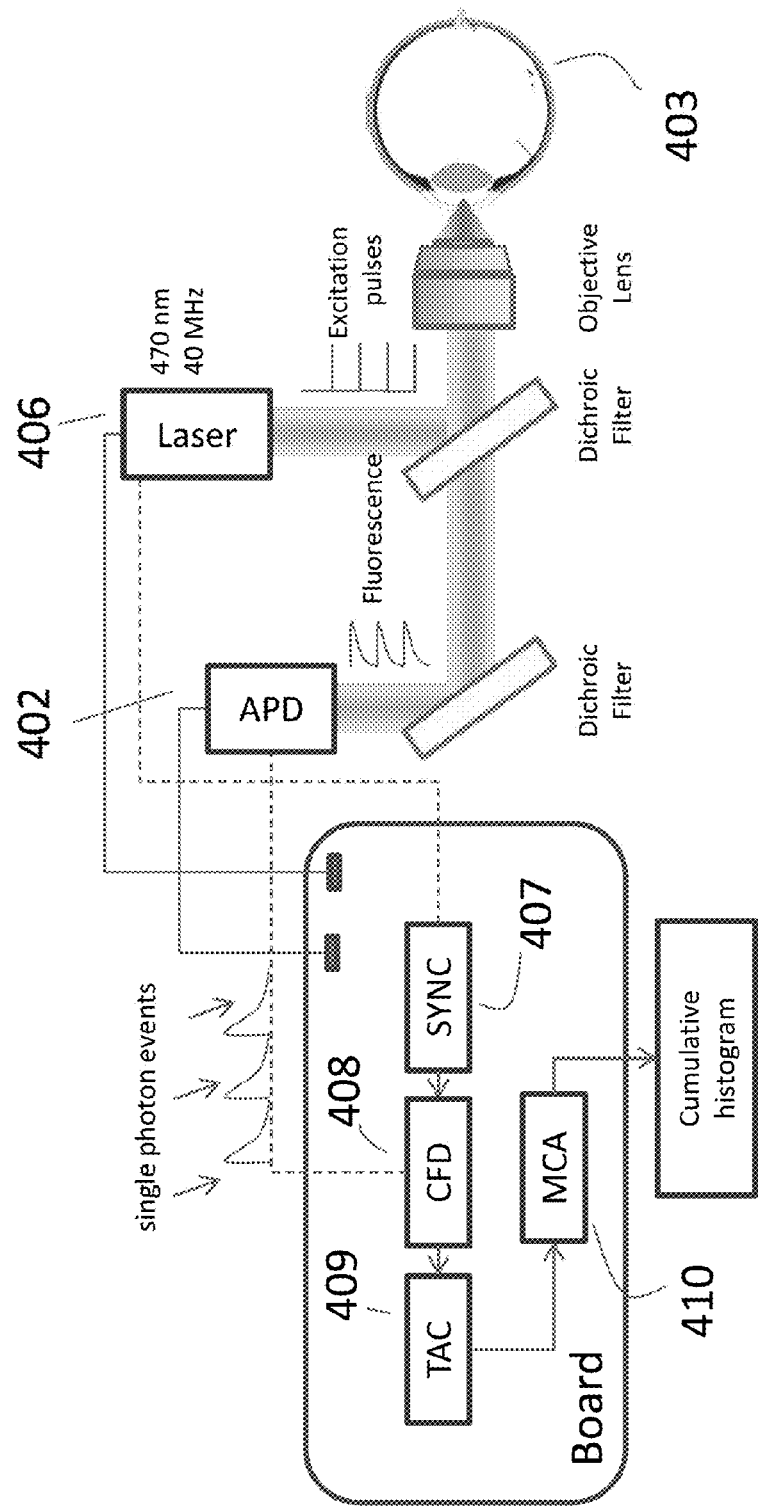
FIG. 4 is a schematic diagram illustrating the use of time-correlation single photon counting, in accordance with an embodiment of the invention.

FIG. 4 is a schematic diagram illustrating the use of time-correlation single photon counting, in accordance with an embodiment of the invention. A pulsed light source 406 excites the sample 403 repetitively. The sample emission is observed by a detector unit avalanche photodiode (APD) 402, while the excitation flashes are detected by a synchronization module (SYNC) 407. A constant fraction discriminator (CFD) 408 responds to only the first photon detected—independent of its amplitude—from the detector 402. This first photon from sample emission is the stop signal for the Time-to-Amplitude Converter (TAC) 409. The excitation pulses trigger the start signals. The Multi-Channel Analyzer (MCA) 410 records repetitive start-stop signals of the single-photon events from the TAC 409, to generate a histogram of photon counts as a function of time channel units. The lifetime is calculated from this histogram. The MCA may be implemented using a dedicated, specialized hardware module and/or using a general purpose computer specially-programmed to perform such tasks; and may be in data communication with a specially-programmed general purpose computer.

In one embodiment according to the invention, a system comprising a fluorescent amyloid-binding compound and a device is intended to aid in the diagnosis of probable Alzheimer's disease in patients who have symptoms and signs consistent with Alzheimer's-type dementia following an adequate clinical examination. The device employs a confocal scanning mechanism combined with a fluorescence lifetime spectroscopy technique. The device enables identification of the anatomical structures of the anterior segments of the eye and discrimination of fluorescent fluorophores based on their optical signatures.

Figure 5:
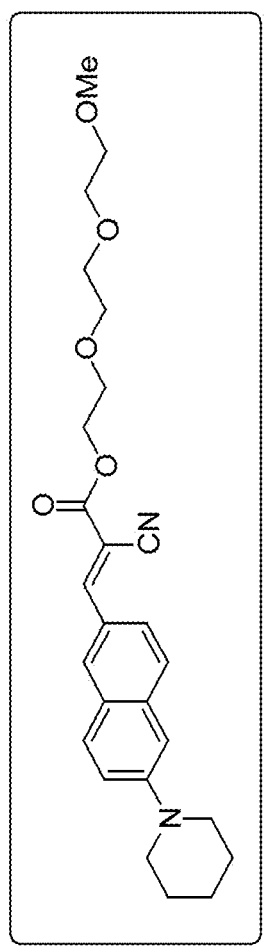
FIG. 5 shows the structure of Compound #11, which may be used as a fluorescent amyloid-binding compound in accordance with an embodiment of the invention.

FIG. 5 shows the structure of Compound #11, which may be used as a fluorescent amyloid-binding compound in accordance with an embodiment of the invention. Compound #11 is a fluorescent compound designed according to the molecular rotor motif, and has been shown to bind to the aggregated beta-amyloid (Aβ) peptide. This, combined with native fluorescence, suggests that Compound #11 is a good candidate for an in vivo marker for Aβ aggregates which have been found in the lens tissue of Alzheimer's patients. The chemical name for Compound #11 is [(E)-2-(2-(2-methoxyethoxy)ethoxy)ethyl-2-cyano-3-(6-(piperidin-1-yl)naphthalen-2-yl)acrylate]. Further information regarding Compound #11 may be found in J. Sutharsan et al., "Rational Design of Amyloid Binding Agents Based on the Molecular Rotor Motif," Chem Med Chem 2010, 5, 56-60, the entire disclosure of which is hereby incorporated herein by reference. Compound #11 has been formulated into an ophthalmic ointment (Compound #11 Ophthalmic Ointment) containing approximately 5 mg/g of Compound #11, 80% petrolatum and 20% mineral oil.

In accordance with an embodiment of the invention, a fluorophore amyloid-binding compound may be applied to an eye of an individual to be tested in any of a variety of different possible forms. For example, the fluorophore amyloid-binding compound may be applied as an ointment, a solution, using a contact lens, by injection, in liquid form, in solid form, by iontophoresis, or by other techniques.

A device in accordance with an embodiment of the invention is designed to detect fluorescence in the time domain with high sensitivity and speed in a confocal detection scheme. The device has two main functionalities: 1) delivery and scanning of the optical beam to locations in the anterior segments of the eye, such as the supranucleus of the lens, using a translation stage and a galvanometer scanner; and 2) identification and discrimination of fluorescent fluorophores based on fluorescence lifetime measurements.

A device in accordance with an embodiment of the invention identifies ocular anatomical structures using an axial scan or z-scan, which is based on the laser excitation of natural fluorescence of ocular tissues along the optic axis of the eye to obtain information on intraocular distances. The z-scan reveals a plot of natural fluorescence intensity as a function of depth that provides information about the location where lifetime measurements are to be performed. The targeted location may, for example, be the supranucleus of the lens in the human eye. The scanning may be completed in seconds, for example in 2 seconds or less, such as in about 0.2 seconds, 0.3 seconds, 0.4 seconds, 0.5 seconds, 0.6 seconds, 0.7 seconds, 0.8 seconds, 0.9 seconds, 1.0 seconds, 1.2. seconds, 1.4 seconds, 1.6 seconds, 1.8 seconds or 2.0 seconds to reduce eye motion artifacts, or another amount of time appropriate to reduce eye motion artifacts. Alternatively or in addition, the device may be used in conjunction with eye-motion tracking to reduce motion artifacts. Piezo drives, linear motors and other controlled motion devices may be used for such a purpose. The axial scan may also allow measurement of the gradient concentration of amyloid-binding compound at ocular interfaces such as tear film/corneal epithelial interface, as well as amyloid-binding compound bioavailability in the aqueous humor.

A device in accordance with an embodiment of the invention identifies fluorescent molecules by performing an xy-scan, in which the sample is raster-scanned with a galvanometer-driven device. The fluorescence lifetime is registered for each location scanned of the human lens and thus a two-dimensional representation of the fluorophore distribution can be evaluated and analyzed based on fluorescence decay rate as well as intensity. A two-dimensional representation of fluorophore distribution based on decay lifetime, which may also, but need not necessarily, include a two-dimensional representation based on fluorescence intensity, is referred to herein as a "fluorescence lifetime image."

In accordance with an embodiment of the invention, fluorescence lifetime measurements are based on repetitively exciting the eye with short laser pulses and recording the subsequent fluorescence emission as a function of time. Since the fluorescence decay time is a characteristic of each fluorescence molecule, one can determine and separate the amyloid-binding compound from natural fluorescence of the lens that is being excited in the sample volume.

In particular, in an embodiment according to the invention, fluorescence lifetime measurements may be obtained by a time correlation single photon counting technique (TCSPC). The scanning speed and data acquisition may be synchronized and executed, for example, in 0.5 seconds to reduce any eye motion artifacts, or another amount of time appropriate to reduce eye motion artifacts. The TCSPC principle is based on the detection of single photons emitted by a pulsed laser and recording of the detection times of the arriving individual photons. When a photon is detected, the time of the corresponding detector pulse is measured. The events are collected in memory for many detected photons. Fluorescence decay lifetimes can be calculated by constructing a histogram from the individual time measurements. A device in accordance with an embodiment of the invention, operating in TCSPC mode, can achieve, for example, count rates of about 107 photons per second. Therefore, 104 photons can be collected in less than 1 ms. Such count rates are important where high speed is necessary to acquire fast scanning information in the lens of the human eye. Other count rates may be used.

A device in accordance with an embodiment of the invention may be designed to obtain specific information from a particular location in the lens of the human eye. Examples of such locations include the supranucleus, lens capsule, nucleus, cornea and aqueous humor.

This is achieved by precise alignment of the subject, knowledge of the ocular anatomy of the eye, and obtaining information of fluorophores in a scanned area in the lens with high specificity and sensitivity. A schematic diagram of an optical platform in accordance with an embodiment of the invention is shown in FIG. 1 (discussed also above). Fluorescence excitation is achieved by a pulsed laser beam that is focused by a high numerical aperture objective lens 101 into the eye 103. The laser may, for example, be pulsed at a repetition rate of about 40 MHz and produce pulses of about 200 picoseconds wide, although other repetition rate and pulse widths may be used. For example, repetition rates from as low as about 1 MHz up to about 240 MHz may be used, and pulse widths of from about 40 picoseconds to about 400 picoseconds may be used. The optical beam then is reflected off a pair of galvanometer scanners and is focused by a high numerical objective lens 101 which is mounted on a translation stage 104. The fluorescence measurements in the supranucleus of the eye are obtained by first aligning the subject eye to the device and performing 1) a z-scan to determine the location of the region of interest (ROI) and 2) an xy-scan to obtain specific information over an area within the supranucleus.

In accordance with an embodiment of the invention, subject alignment consists of identifying the focal plane of the objective lens as a reference starting point of the measurement. A light emitting diode (LED), which is used also as a fixation target, is focused by the objective lens 101 onto the cornea of the eye 103 in the shape of a ring. A camera is used to visualize the reflection of the ring off the surface of the cornea. Once this is achieved, the scanning of the eye can be performed to obtain the necessary information.

In accordance with an embodiment of the invention, identification of the anatomical structures of the lens is performed by scanning the objective lens 101 along the optical axis (on axis) using a translation stage 104. The z-scan involves the excitation of the natural fluorescence with the laser source and identification of the anatomical structures of the anterior segments such as the cornea, lens capsule and supranucleus region of the lens and their relative distances. In addition, the scan can provide information about the pharmacokinetics of exogenous amyloid-binding compound applied to the eye.

In accordance with an embodiment of the invention, once the region of interest is identified in the eye using the z-scan measurement, a planar scan (xy-scan) in the plane perpendicular to the axial scan is performed using the galvanometer mirrors. To ensure allocation of the measured fluorescence decay curves to the corresponding site of the two-dimensional scanning, the galvanometer mirrors are synchronized with the data acquisition board for TCSPC measurements. An xy-scan may entail, for example, scanning a region 50 by 50 μm in the supranucleus of a human eye in 0.5 seconds and extracting lifetime decay values. It will be appreciated that regions of other sizes and locations, and times of scans, may be used.

In accordance with an embodiment of the invention, detection is achieved with TCSPC through a confocal configuration with a fast avalanche photodiode detector (APD) 102. Fluorescence from the excited molecules is collected with the same objective lens 101 as the excitation laser, filtered after the dichroic mirror with an additional bandpass filter to reject remaining scattered laser light and passed through a small aperture to enable confocal detection. With fast-timing option, the APD 102 may, for example, provide timing resolution better than 50 picoseconds Full Width Half Maximum with photon detection efficiency of 49% at 550 nm, although other timing resolutions and photon detection efficiencies may be used.

An illustration of the data acquisition and electronics behind TCSPC is shown in FIG. 4 (discussed also above), in accordance with an embodiment of the invention. The pulsed light source 406 excites the sample 403 repetitively at (for example) a 40 MHz repetition rate while the excitation pulses are detected by a synchronization (SYNC) module 407 which is set (for example) also at 40 MHz. The excitation pulses trigger the start signals. A constant fraction discriminator (CFD) 408 responds to only the first photon detected from the detector, independent of its amplitude. This first photon from sample emission is the stop signal for the Time-to-Amplitude Converter (TAC) 409. When the APD 402 detects a photon, a short pulse is created at the output of the PMT. The pulse is "cleaned" by the CFD 408 and enters the TAC 409 as a "stop" pulse. Once the stop pulse (i.e., the first arriving photon) has been detected, the voltage ramp is stopped and the voltage value (equivalent to the time difference between the start and stop pulses) is transmitted to the Multi-Channel Analyzer (MCA) 410. The MCA 410 records repetitive start-stop signals of the single-photon events from the TAC 409 and increments the counts in the channel in correspondence with the detected voltage (time). This process is repeated with each pulse and eventually, after many cycles, a histogram of photon counts as a function of time channel units is generated. The histogram represents the fluorescence intensity as a function of time, from which the fluorescence decay lifetime is obtained.

In accordance with an embodiment of the invention, the data acquisition may be performed using the PicoHarp 300 TCSPC (PicoQuant, GmbH, Berlin, Germany) PC-board working in the special Time-Tagged Time-Resolved Mode, which stores all relevant information for every detected photon for further data analysis. In particular, every photon arrival time is recorded at the detector in synchronization with the laser excitation pulse and the position of the sample and the number of the detection channel. The sync rate of the acquisition board may, for example, be set at 40 MHz with a time resolution of 4 picoseconds and channel count depth of 16 bit (other sync rates, time resolutions and channel count depths may be used).

In accordance with an embodiment of the invention, the software acquisition, which may be performed using Sym-PhoTime, (PicoQuant, GmbH, Berlin, Germany), may be controlled via a TCP/IP network and synchronized with both the galvanometer scanner and the acquisition board through TTL signals to define the line and the frame of the image. SymPhoTime in LSM command mode may, for example, record and display the fluorescence lifetime and intensity images.

In accordance with an embodiment of the invention, the fluorescence lifetime may be registered for each location scanned within the human lens, and thus a two-dimensional representation of the fluorophore distribution can be evaluated and analyzed based on fluorescence decay rate and intensity. A constructed color coded image based on fluorescence lifetime decay can be superimposed on the intensity image to facilitate clinical interpretation. The calculation of a fluorescence lifetime image may be done by sorting all photons which correspond to one pixel into a histogram, which is then fitted to an exponential decay function to extract the lifetime information. This procedure is then repeated for every pixel in the image. The software algorithm may fit the data to multi-exponential decay functions using tail-fitting as well as numerical re-convolution. As the fitting procedure relies on the quality of the start parameters for the fit, frequency count of photons of specific decay rates that is indicative of specific fluorophores over an area scan can be extracted directly from the image. The foregoing algorithms may be implemented by computer, and may involve displaying data on a two-dimensional display such as a computer monitor.

In one embodiment according to the invention, an average intensity associated with a specific lifetime decay may be used as a measure of aggregation of amyloid proteins. That is, a parameter can be created by averaging a fluorescent intensity, associated with a specific lifetime decay, over a specific area. This parameter can be used as a measure of aggregation, for example to monitor progression of a disease in an individual based on changes in the parameter. Such a parameter may be determined by computer or other specialized hardware.

Figure 6:
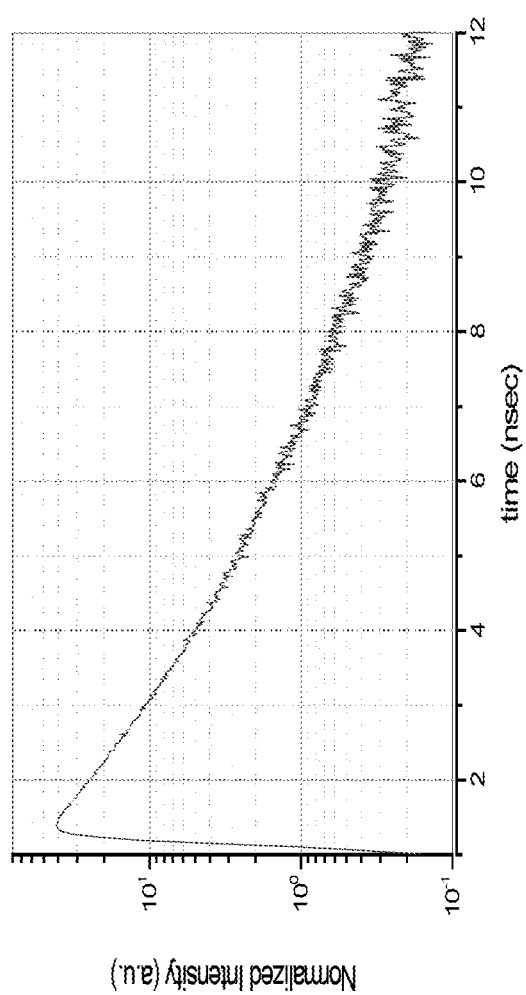
FIG. 6 is a fluorescent histogram of the fluorescent amyloid-binding compound Compound #11, obtained by a device in accordance with an embodiment of the invention.

A fluorescent histogram of the fluorescent amyloid-binding compound Compound #11 is shown in FIG. 6, obtained by a device in accordance with an embodiment of the invention. Single exponential fitting results in a lifetime decay rate of 2 nsec.

Figure 7:
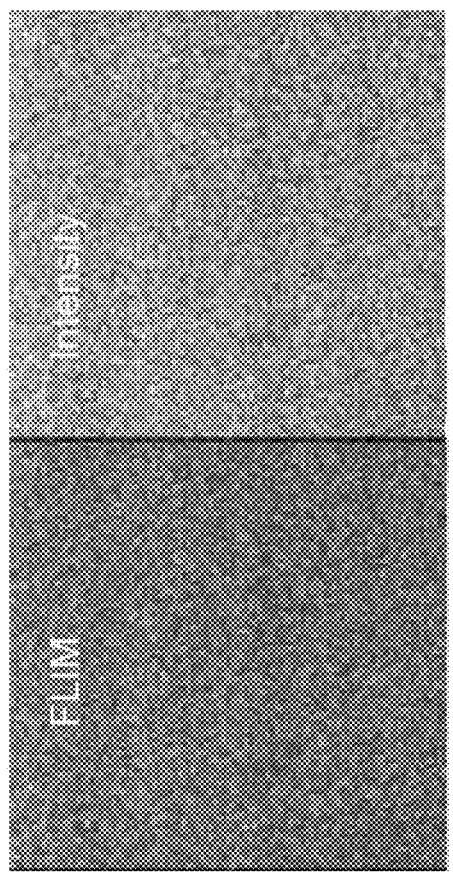
FIG. 7 is a diagram of a fluorescence lifetime image of Compound #11 and its corresponding intensity image, obtained in accordance with an embodiment of the invention.

FIG. 7 shows a fluorescence lifetime image of Compound #11 and its corresponding intensity image, obtained in accordance with an embodiment of the invention. The images are 100×100 pixels obtained in 0.5 seconds and represent a scanning area of 50×50 microns.

An embodiment according to the invention uses a fluorescence time domain technique to detect and resolve fluorophores based on their lifetime signature. By combining fluorescence intensity and lifetime measurements, an extra dimension of information is obtained to discriminate among fluorescent labels. In vitro studies discussed in Experiment #1 demonstrate the capability of an embodiment according to the invention in differentiating fluorescent fluorophores based on their lifetime decay signature. Further, the pharmacokinetics studies on rabbit eyes discussed in Experiment #2 show detectable fluorescence signal of the fluorescent amyloid-binding compound Compound #11 in the supranucleus of the lens. More important, the signal detected in the lens of the rabbit eye was easily identified and assigned to the amyloid-binding compound itself.

It will be understood by a person skilled in the art that any method presented herein (as well as individual steps thereof and combinations of several subsequent steps of these methods), in particular the technical steps involving the collection and optionally processing of relevant data, the comparison of the data thus obtained with the normal control values and/or the finding of any significant deviation during that comparison, may be performed ahead of, independent thereof and in preparation of a subsequent, separate diagnosis step, i.e., prior to attributing a potential deviation between the values obtained and the normal control value(s) to a particular amyloidogenic disorder such as Alzheimer's disease (the actual diagnosis). These methods (including individual steps as well as combinations of several subsequent steps of these methods) performed ahead of, independent thereof and in preparation of a subsequent, separate diagnosis are specifically contemplated as individual embodiments of the invention.

In accordance with an embodiment of the invention, various sub-components of the system may be supplied by existing suppliers. For example, excitation sources may be the Picosecond Pulsed Laser, LDH series, sold by PicoQuant of Berlin, Germany; the Picosecond Diode Laser, BDL series, sold by Becker & Hickl of Berlin, Germany; or the Picosecond Light Pulser, PLP series, sold by Hamamatsu Photonics of Hamamatsu, Japan. Data acquisition may be performed using the TCSPC module, PicoHarp 300, sold by PicoQuant, Berlin, Germany; the TCSPC module, SPC series, sold by Becker & Hickl, Berlin, Germany; or the Synchronous Delay Generator, C10647 sold by Hamamatsu Photonics, Hamamatsu, Japan. Photon Counting Detectors may be the Detector Unit, PMA series, sold by PicoQuant, Berlin, Germany; the Detector Unit, ID-100 Series, sold by Becker & Hickl, Berlin, Germany; or the Streakscope (C10627 series, sold by Hamamatsu Photonics, Hamamatsu, Japan). It will be appreciated that other excitation sources, data acquisition modules and photon counting detectors may be used.

Portions of the above-described embodiments of the present invention can be implemented using one or more computer systems. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, a tablet computer, a single circuit board computer or a system on a chip. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, touch screens and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, at least a portion of the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement at least a portion of the various embodiments of the invention discussed above. The computer readable medium or media can be transportable, such that the program or programs stored thereon can be loaded onto one or more different computers or other processors to implement various aspects of the present invention as discussed above.

In this respect, it should be appreciated that one implementation of at least a portion of the above-described embodiments comprises at least one computer-readable medium encoded with a computer program (e.g., a plurality of instructions), which, when executed on a processor, performs some or all of the above-discussed functions of these embodiments. As used herein, the term "computer-readable medium" encompasses only a computer-readable medium that can be considered to be a machine or a manufacture (i.e., article of manufacture). A computer-readable medium may be, for example, a tangible medium on which computer-readable information may be encoded or stored, a storage medium on which computer-readable information may be encoded or stored, and/or a non-transitory medium on which computer-readable information may be encoded or stored. Other non-exhaustive examples of computer-readable media include a computer memory (e.g., a ROM, a RAM, a flash memory, or other type of computer memory), a magnetic disc or tape, an optical disc, and/or other types of computer-readable media that can be considered to be a machine or a manufacture.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Experiment #1

In Vitro Study of Neuroptix Fluorescent Ligand with Beta Amyloid Peptide (1-42)

Figures 8A, 8B:
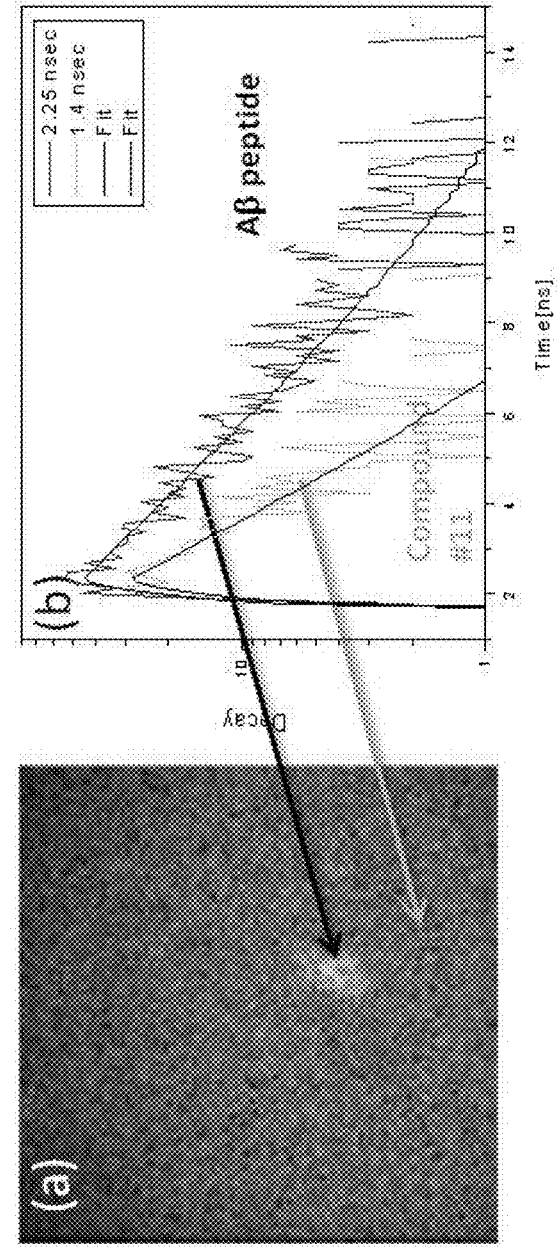
FIG. 8A is a fluorescence lifetime image showing amyloid-binding compound and amyloid-binding compound bound to aggregate peptide in accordance with an embodiment of the invention.
FIG. 8B is a diagram showing the corresponding fluorescence lifetime histograms for the amyloid-binding compound and amyloid-binding compound bound to aggregate peptide of the fluorescence lifetime images of FIG. 8A, in accordance with an embodiment of the invention.

In accordance with an embodiment of the invention, in vitro studies on aggregated Aβ peptides bound to Compound #11 were performed. Fluorescence lifetime measurements of Compound #11 with aggregated Aβ peptide were performed using a device in accordance with an embodiment of the invention. FIG. 8A is a fluorescence lifetime image showing Compound #11 and Compound #11 bound to aggregated Aβ peptide, with their corresponding fluorescence lifetime histograms shown in FIG. 8B, in accordance with an embodiment of the invention. By fitting the lifetime histograms, the decay rates are determined. The results demonstrate the superior performance of an embodiment in accordance with the invention that is capable of differentiating between fluorophores of lifetime difference of as little as 0.85 nsec with low level of photon detection. An experimental description follows.

The purpose of this in vitro study was to identify the optical signature of the Compound #11 amyloid-binding compound, and to characterize its fluorescence properties when bound to aggregated Aβ peptide. In particular, the objectives of the study were: 1) characterization of Compound #11 lifetime decay rates; and 2) ability to detect and differentiate between Compound #11 bound and un-bound to beta amyloid (Aβ) peptides.

Device:

The Neuroptix SAPPHIRE II device (Neuroptix Corporation, Acton, Mass., U.S.A.) is a purpose built device for clinical studies in humans, which was adapted for in vitro measurements for this experiment. It employs a confocal scanning mechanism combined with fluorescence lifetime spectroscopy that allows differentiation of fluorophores. The device allows 1) scanning of the optical beam to specific locations in the anterior segments of the eye, such as the supranucleus and 2) identification of fluorescent fluorophores based on fluorescence lifetime measurements.

Method—Aggregated Aβ Peptides Preparation:

Aggregated Aβ peptide was prepared by dissolving Aβ(1-42) in PBS pH 7.4 to a final concentration of 100 μM. This solution was magnetically stirred at 1200 rpm for 3 days at room temperature. The 100 μM Aβ(1-42) stock solution in PBS was aliquoted and frozen at −80° C. for up to 4 weeks without noticeable change in its property. 150 μL of pre-aggregated Aβ(1-42) was added to 2.85 mL of Compound #11 to attain a final concentration of 5 μM Aβ(1-42) and 4 μM of Compound #11. The solution was transferred to 5 mL vial and the fluorescence measurements were performed at 25° C.

Experiment and Results—

The sample consisting of Compound #11 was placed in front of the Neuroptix SAPPHIRE II Device. Once the location of the scan in the sample was determined, a raster scan was performed to obtain fluorescence lifetime measurements. FIG. 8A shows an image (200×200 pixels) with a scan range of 100 μm×100 μm obtained in 1 second acquisition time. The image is shaded to represent lifetime decays. The shading that makes up most of the image background represents a lifetime decay of 1.4 nsec, which corresponds to that of the fluorescence amyloid-binding compound. The spot detected in the image is that of the aggregated Aβ peptide representing a lifetime decay of 2.25 nsec. The plot in FIG. 8B shows the fluorescence decay rates calculated for both the Compound #11 and that of the Compound #11 bound to aggregated Aβ peptide.

Conclusion

In vitro fluorescence lifetime measurements of Compound #11 with aggregated Aβ peptide were performed with Neuroptix SAPPHIRE II Device. Based on fluorescence lifetime decay rates, bound and unbound peptide to Compound #11 can be resolved. The results demonstrate the superior performance of the SAPPHIRE II Device that is capable of differentiating between fluorophores with 0.85 nsec difference in lifetime just by detection level of a few hundred photons.

Experiment #2

Ocular Pharmacokinetics Study in Dutch-Belted Rabbits

In accordance with an embodiment of the invention, in vivo pharmacokinetics studies of Compound #11 in rabbit eyes were performed using a device in accordance with an embodiment of the invention. FIG. 9A is a plot of the frequency count of photons of specific decay rates measured on two rabbits dosed with the amyloid-binding compound along with a controlled rabbit. The frequency count of photons of specific decay rates that pertained to the fluorescent amyloid-binding compound (Compound #11) was calculated from the fluorescence histogram (FIG. 9B), in accordance with an embodiment of the invention. The results demonstrate the capability of the amyloid-binding compound to penetrate the cornea and be detected by the device in the lens of rabbit eyes. An experimental description follows.

Introduction

Ocular pharmacokinetic investigation of dose response via topical administration of fluorescence amyloid-binding compound was performed in Dutch-belted rabbits. The rabbits were tested each day over a 4 day period using Compound #11 amyloid-binding compound in an ointment. Two animals were dosed in the right eye with Compound #11 (0.5%) in ointment form. One animal was untreated and used as control animal. The animals were dosed at specific time points for four days and tested with SAPPHIRE II system for fluorescence intensity and lifetime measurements at the beginning and end of each day.

The results demonstrate:

1) Detectable fluorescence signal was achieved with concentration of 5 mg/g Compound #11 in ointment form after repetitive topical administration.

2) The fluorescence measurements performed at the beginning and at the end of the day and over a period of four days show increase of Compound #11 fluorescence in the lens nucleus of the rabbit eyes.

Methods:

Ocular measurements were performed at the time intervals and dose concentrations stated in the table below.

TABLE 1

Animal Group tested, dosages administered, and measurement times

| Group | Treatment | # of Animals | Dosage by Toxikon | Ocular Measurements by Sponsor |
|---|---|---|---|---|
| 1 | 5 mg/g (Ointment) | 2 | Ointment dosed for 4 days at 830, 1130 and 1430 | SAPPHIRE II tests at the beginning and end of each day |
| Control | — | 1 | | SAPPHIRE II tests at the beginning and end of each day |

The study was staggered over four days and performed in a single location and on asingle instrument. Tests were performed in a dimly lit room dedicated to the study.

All animals were dosed with Compound #11 via topical ocular application and tested in the right eye. Animals were anesthetized and manually held on a platform in front of the Neuroptix SAPPHIRE II device. Gross positioning was done by the animal handler, and fine tuning of the measurement location was done by the Neuroptix SAPPHIRE II operator. Once aligned, the SAPPHIRE II operator initiated the measurement sequence. Baseline measurements were made on the animals before dosing, and then at the beginning and end of each day (Table 1).

Experimental Design and Dosage:

Fluorescence lifetime and intensity measurements were performed in the eye at the beginning and at the end of each day. The measurements entailed scanning the rabbit eye axially (z-scan) to obtain inter-ocular information and a planar scan (xy-scan) to perform lifetime decay measurements in a certain region of the eye, which is the lens nucleus in this case.

Once the location of interest was identified, Time Correlation Single Photon Counting (TCSPS) was initiated while performing the xy-scan. The fluorescence lifetime images were then obtained where the decay lifetime histogram was obtained for each pixel location. The calculated decay times were color coded in the fluorescence lifetime image. Each measurement was performed three times. The frequency count of photons of specific decay rates were calculated from the decay rates frequency that of the Compound #11 signature obtained in the xy-scan and averaged over the three measurements. Calibration measurements were taken once a day on a fluorescence dye and showed repeatable performance with no apparent drift throughout the study. The device was specifically designed for human use but the platform was slightly modified for holding the rabbits.

Dosing was performed by Toxikon staff via topical ocular application into the right eye of each animal.

Group 1: Animals were anesthetized with subcutaneous injection of Dexdomitor (0.5 mg/kg), Ketamine (5 mg/kg). A ribbon of ointment approximately ½ inch long was then applied to the lower right eyelid of each animal in the test group three times a day for four days.

Control: For the control group, one animal was handled in the same way as the animals in the test groups except no ointment or solution was administered to the eye.

Figure 10A:
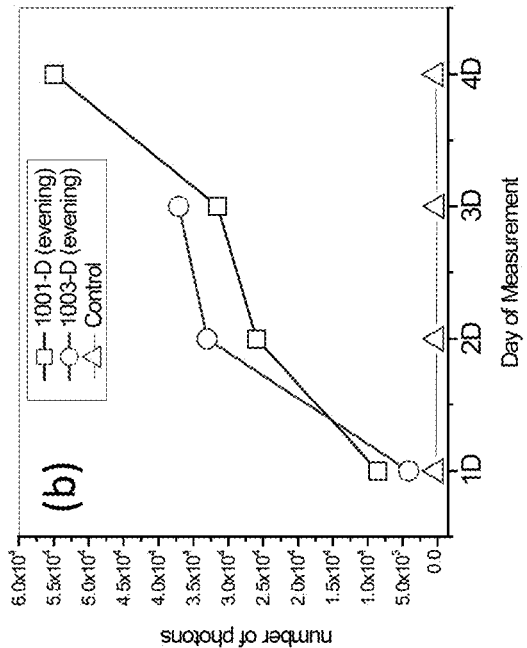
FIGS. 10A and 10B are plots showing the frequency of photons of a specific decay rate that pertain to the fluorescent amyloid-binding compound Compound #11 measured in the morning for baseline and at the end of the day after being dosed during a study of rabbits, in an experiment in accordance with an embodiment of the invention.
Figure 10B:
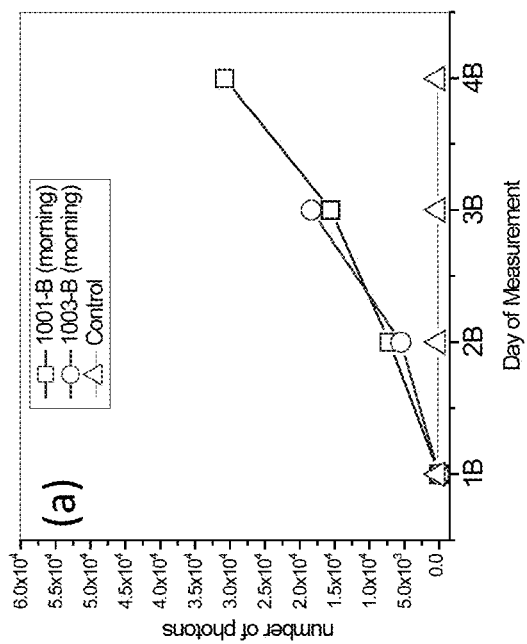

Summary of Results:

Fluorescence intensity and lifetime measurements of the amyloid-binding compound in the eye were performed at the beginning (morning) and end (evening) of each day. FIGS. 10A and 10B are plots showing the frequency count of photons of specific decay rates that pertain to Compound #11 measured in the morning for baseline and at the end of the day after being dosed during the four day study period in the lens nucleus of the five rabbits. FIG. 10A is a plot for the morning measurements, and FIG. 10B is a plot for the evening measurements, both being on rabbits dosed with Compound #11 Ophthalmic Ointment. The measurements on the two rabbits (1002 and 1003), which were dosed with Compound #11 Ophthalmic Ointment, show significant increase in fluorescence signal in the nucleus of the eye. FIGS. 10A and 10B show that after three dosages each day with three hours separation, a cumulative fluorescence signal is measured along the 4 day study period.

In FIGS. 11A and 11B are two fluorescence lifetime images taken at baseline and after the end of the fourth day of the study with animal 1003. The baseline measurement exhibited a black image indicative of no presence of Compound #11 in the lens of the eye. After four days, an xy-scan revealed a lifetime image with a decay rate of 2 nsec (displayed in gray) which is a signature of the fluorescence lifetime. The difference in signal collected between the two rabbits can be attributed to the dosing variation by the technician and blinking by the animal.

CONCLUSION

The primary objective was achieved with Compound #11 Ophthalmic Ointment at a concentration of 5 mg/g. Repetitive topical administration of Compound #11 tended to accumulate in the nucleus after several hours of application and tended to stay there for at least 12 hours.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for detecting an amyloid protein in an eye of a mammal, the method comprising:
    illuminating the eye with a light source having at least one of a wavelength property, a polarization property or a combination thereof, each appropriate to produce fluorescence in at least an amyloid-binding compound when the amyloid-binding compound is bound to the amyloid protein, the amyloid-binding compound having been introduced to the eye and specifically binding to the amyloid protein indicative of the amyloidogenic disorder;
    receiving light including fluorescence produced as a result of the illuminating the eye; and
    determining a time decay rate of fluorescence for at least the fluorescence produced by the amyloid-binding compound bound to the amyloid protein, the determining permitting distinguishing of the presence of the amyloid-binding compound bound to the amyloid protein in the eye based on at least the time decay rate, the determining comprising performing a time correlation single photon counting of fluorescence produced by the eye;
    wherein the distinguishing the presence of the amyloid-binding compound bound to the amyloid protein comprises distinguishing the amyloid-binding compound bound to the amyloid protein from background autofluorescence of eye tissues, autofluorescence of other non-specific particles and unbound amyloid-binding compound.

2. A method according to claim 1, further comprising determining an intensity of fluorescence for at least the fluorescence produced by the amyloid-binding compound bound to the amyloid protein.

3. A method according to claim 2, further comprising determining a quantity of the amyloid-binding compound bound to the amyloid protein, based on at least one of the intensity and the time decay rate.

4. A method according to claim 1, wherein illuminating the eye with the light source comprises illuminating the eye with a pulsed laser.

5. A method according to claim 1, comprising illuminating the eye with light at a repetition rate of between about 1 MHz and about 240 MHz.

6. A method according to claim 1, comprising illuminating the eye with light comprising pulse widths of between about 40 picoseconds to about 400 picoseconds wide.

7. A method according to claim 1, comprising illuminating the eye with light at a repetition rate of about 40 MHz and with a pulse width of about 200 picoseconds wide.

8. A method according to claim 1, further comprising:
    determining a location of an ocular interface of the eye based on an increase in a fluorescent signal due to natural fluorescence emitted from tissues of the eye.

9. A method according to claim 1, further comprising:
    sampling at least one region of interest in the eye using illumination by the light source, the sampling comprising illuminating at least one of a point or points, a plane or planes, or a volume or volumes within the at least one region and detecting the fluorescence emissions.

10. A method according to claim 9, wherein the sampling comprises sampling different locations across more than one region of the eye.

11. A method according to claim 1, further comprising:
    performing planar scans of the eye using the light source, in successive planes along a perpendicular axis extending depthwise into the eye.

12. A method according to claim 1, further comprising determining a location of a supranucleus of the eye based on at least one of: (i) a distance away from an anatomical structure of the eye and (ii) a detection of a change in an intensity measurement.

13. A method according to claim 1, further comprising distinguishing at least one of a presence and a quantity of more than one of the following: the amyloid-binding compound; the amyloid-binding compound bound to the amyloid protein; and the amyloid protein.

14. A method according to claim 1, wherein the amyloid protein comprises an aggregate.

15. A method according to claim 1, wherein the amyloid protein comprises a pre-amyloid protein aggregate.

16. A method according to claim 1, wherein the amyloid protein comprises beta-amyloid.

17. A method according to claim 1, wherein the amyloidogenic disorder comprises Alzheimer's disease.

18. A method according to claim 1, wherein the amyloid-binding compound comprises a molecular rotor.

19. A method according to claim 1, wherein the amyloid-binding compound comprises at least one of: a Congo red or Congo red derivative amyloid-binding compound; a Chrysamine amyloid-binding compound; a Chrysamine derivative amyloid-binding compound; a Chrysamine G or Chrysamine G derivative amyloid-binding compound; a Thioflavin T or Thioflavin T derivative amyloid-binding compound; and a Thioflavin S or Thioflavin S derivative amyloid-binding compound.

20. A method according to claim 1, comprising distinguishing at least the presence of the amyloid protein based only on detected fluorescence.

21. A method according to claim 1, further comprising determining a rate of delivery of the amyloid-binding compound to the eye based on detected fluorescence.

22. A method according to claim 1, further comprising determining the average number of photons with a specific decay rate in a certain area of the eye.

23. A method according to claim 1, further comprising determining a spatial distribution of amyloid-binding compound delivered to the eye based on detected fluorescence.

24. A method according to claim 1, further comprising determining a gradient of concentration of the amyloid-binding compound at an interface of the cornea of the eye based on detected fluorescence.

25. A method according to claim 1, further comprising determining at least one of a spatial distribution of the amyloid-binding compound and a temporal distribution of the amyloid-binding compound in the aqueous humor of the eye based on detected fluorescence.

26. A method according to claim 1, further comprising determining at least one dimension of an anatomical structure or substructure of the eye based on natural fluorescence excitation of at least a portion of the anatomical structure or substructure.

27. A method according to claim 26, wherein determining the at least one dimension comprises at least one of determining a thickness of the structure or substructure, determining a shape of the structure or substructure, and determining a distance between one or more structure or substructures of the eye.

28. A method according to claim 1, further comprising detecting fluorescence produced by the eye using a photodetector device.

29. A method according to claim 28, wherein the photodetector device comprises at least one of a photodiode, a photomultiplier, a charge-coupled device and an intensified charge-coupled device.

30. A method according to claim 29, wherein the photodetector device comprises a fast avalanche photodiode detector.

31. A method according to claim 1, wherein performing the time correlation single photon counting comprises pulsing the light source and determining the time decay rate of fluorescence based on a distribution of photon counts as a function of time channel units.

32. A method according to claim 1, comprising:
scanning within the eye to determine excited natural fluorescence and thereby to determine at least one region of interest in the eye; and
sampling at least one region of interest in the eye using illumination by the light source, the sampling comprising illuminating at least one of a point or points, a plane or planes, or a volume or volumes within the at least one region;
the sampling being to determine an intensity of fluorescence and a time decay rate of fluorescence for at least the fluorescence produced by the amyloid-binding compound bound to the amyloid protein within the at least one sampled region.

33. A method according to claim 1, comprising:
performing an axial scan depthwise into the eye to determine excited natural fluorescence along each point of the axial scan and thereby to determine at least one location of interest in the eye; and
performing planar scans of the eye using the light source, in successive planes perpendicular to the direction of the axial scan, to determine an intensity of fluorescence and a time decay rate of fluorescence for at least the fluorescence produced by the amyloid-binding compound bound to the amyloid protein at each point of each of the planar scans.

34. A method according to claim 1, wherein the method enables a real time search within the eye for the amyloid protein indicative of the amyloidogenic disorder.

35. A method according to claim 1, further comprising illuminating the eye with light of an appropriate wavelength for a peak region of a fluorescent excitation spectrum for the amyloid-binding compound bound to the amyloid protein in the eye; and
detecting light received from the eye of an appropriate wavelength for a peak region of a fluorescent emission spectrum for the amyloid-binding compound bound to the amyloid protein in the eye.

36. A method according to claim 35, wherein the amyloid-binding compound is Compound #11.

37. A method according to claim 35, wherein the excitation spectrum has a peak of about 470 nm, the illuminating of the eye being at a wavelength within plus or minus about 20 nm of the peak of the excitation spectrum, and wherein the emission spectrum has a peak of about 580 nm, the detecting of light received from the eye being at a wavelength within plus or minus about 20 nm of the peak of the emission spectrum.

38. A method according to claim 1, wherein the amyloid protein is indicative of an amyloidogenic disorder.

39. A method according to claim 1, wherein the method permits distinguishing between at least two different fluorophores with similar fluorescence spectra based on at least the time decay rate, the similar fluorescence spectra comprising at least one of a significant overlap in emission spectra and excitation spectra.

40. A method according to claim 1, further comprising representing a distribution of at least one of a fluorescent intensity and a lifetime decay of at least one fluorophore in two dimensions.

41. A method according to claim 1, further comprising determining a number of photons bound and a number of photons unbound based on at least one of a fluorescent intensity and a lifetime decay of at least one fluorophore.

42. A method according to claim 41, further comprising representing in two dimensions a distribution of fluorescent intensity and lifetime decay of bound amyloid-binding compound to protein and unbound amyloid-binding compound to protein.

43. A method according to claim 42, further comprising synchronizing the representing in two dimensions with at least one of a scanner and a laser.

44. A method according to claim 1, further comprising determining a parameter by averaging a fluorescent intensity, associated with a specific lifetime decay, over a specific area of the eye.

45. A method according to claim 1, further comprising aligning an alignment light source with the eye along a confocal path to determine a reference point within the eye.

46. A method of diagnosing an amyloidogenic disorder or a predisposition thereto in a mammal, the method comprising:
illuminating an eye of the mammal with a light source having at least one of a wavelength property, a polarization property or a combination thereof, each appropriate to produce fluorescence in at least an amyloid-binding compound when the amyloid-binding compound is bound to an amyloid protein indicative of the amyloidogenic disorder, the amyloid-binding compound having been introduced to the eye and specifically binding to the amyloid protein indicative of the amyloidogenic disorder;
receiving light including fluorescence produced as a result of the illuminating the eye; and
determining a time decay rate of fluorescence for at least the fluorescence produced by the amyloid-binding compound bound to the amyloid protein, the determining permitting distinguishing of the presence of the amyloid-binding compound bound to the amyloid protein in the eye based on at least the time decay rate, the determining comprising performing a time correlation single photon counting of fluorescence produced by the eye;
wherein an increase in binding of the amyloid-binding compound to the amyloid protein in the eye compared to a normal control level of binding indicates a diagnosis of an amyloidogenic disorder, or a risk of developing an amyloidogenic disorder in the mammal;

wherein the distinguishing the presence of the amyloid-binding compound bound to the amyloid protein comprises distinguishing the amyloid-binding compound bound to the amyloid protein from background autofluorescence of eye tissues, autofluorescence of other non-specific particles and unbound amyloid-binding compound.

47. A method according to claim 46, wherein the amyloidogenic disorder is Alzheimer's disease.

48. A method for identifying an anatomical structure of an eye of a mammal, the method comprising:

illuminating the eye with a light source having at least one of a wavelength property, a polarization property or a combination thereof, each appropriate to produce natural fluorescence in the anatomical structure of the eye; and determining a location within the eye of greatest change in intensity of the natural fluorescence produced by the illuminating with the light source, the determining permitting identifying of the anatomical structure based on the location of greatest change in intensity of the natural fluorescence;

the method further comprising:

using the light source to detect in the eye of the mammal an amyloid protein indicative of an amyloidogenic disorder;

illuminating the eye of the mammal with the light source, the light source further comprising at least one of a wavelength property, a polarization property or a combination thereof, each appropriate to produce fluorescence in at least an amyloid-binding compound when the amyloid-binding compound is bound to the amyloid protein indicative of the amyloidogenic disorder, the amyloid-binding compound having been introduced to the eye and specifically binding to the amyloid protein indicative of the amyloidogenic disorder;

receiving light including fluorescence produced as a result of the illuminating the eye; and determining a time decay rate of fluorescence for at least the fluorescence produced by the amyloid-binding compound bound to the amyloid protein, the determining permitting distinguishing of the presence of the amyloid-binding compound bound to the amyloid protein in the eye based on at least the time decay rate, the determining comprising performing a time correlation single photon counting of fluorescence produced by the eye;

wherein the distinguishing the presence of the amyloid-binding compound bound to the amyloid protein comprises distinguishing the amyloid-binding compound bound to the amyloid protein from background autofluorescence of eye tissues, autofluorescence of other non-specific particles and unbound amyloid-binding compound.

49. A method according to claim 48, wherein the anatomical structure comprises an anatomical structure of the anterior segment of the eye.

50. A method according to claim 48, wherein the identifying of the anatomical structure comprises determining the location of an anatomical interface.

51. A method according to claim 50, wherein the determining the location of the anatomical interface comprises determining the location of an interface of the lens capsule of the eye based on determining a location of the greatest increase in intensity of the natural fluorescence.

52. A method according to claim 48, wherein the identifying of the anatomical structure comprises determining at least one of a corneal thickness, corneal shape, aqueous humor depth, lens shape, lens thickness, and at least one of a thickness and a shape of at least one substructure of the lens of the eye based on natural fluorescence produced by the light source in the eye.

53. A method according to claim 52, wherein the at least one substructure of the lens comprises at least one of a lens capsule, a cortex, a supranucleus and a nucleus of the eye.

54. A method according to claim 48, wherein the identifying of the anatomical structure comprises determining an intra-ocular distance between at least two anatomical structures of the eye.

55. A method according to claim 48, wherein the method enables a real time search within the eye for the amyloid protein indicative of the amyloidogenic disorder.

56. A method according to claim 48, further comprising illuminating the eye with light of an appropriate wavelength for a peak region of a fluorescent excitation spectrum for the amyloid-binding compound bound to the amyloid protein in the eye; and detecting light received from the eye of an appropriate wavelength for a peak region of a fluorescent emission spectrum for the amyloid-binding compound bound to the amyloid protein in the eye.

57. A method according to claim 56, wherein the amyloid-binding compound is Compound #11.

58. A method according to claim 56, wherein the excitation spectrum has a peak of about 470 nm, the illuminating of the eye being at a wavelength within plus or minus about 20 nm of the peak of the excitation spectrum, and wherein the emission spectrum has a peak of about 580 nm, the detecting of light received from the eye being at a wavelength within plus or minus about 20 nm of the peak of the emission spectrum.

* * * * *